(12) United States Patent
Sato

(10) Patent No.: US 12,383,163 B2
(45) Date of Patent: Aug. 12, 2025

(54) TEST JIG, TEST DEVICE, AND TEST METHOD

(71) Applicants: NEC Corporation, Tokyo (JP); NEC Platforms, Ltd., Kawasaki (JP)

(72) Inventor: Hideki Sato, Kanagawa (JP)

(73) Assignees: NEC CORPORATION, Tokyo (JP); NEC Platforms, Ltd., Kanagawa (JP)

(*) Notice: Subject to any disclaimer, the term of this patent is extended or adjusted under 35 U.S.C. 154(b) by 138 days.

(21) Appl. No.: 18/281,815

(22) PCT Filed: Mar. 17, 2021

(86) PCT No.: PCT/JP2021/010837
§ 371 (c)(1),
(2) Date: Sep. 13, 2023

(87) PCT Pub. No.: WO2022/195766
PCT Pub. Date: Sep. 22, 2022

(65) Prior Publication Data
US 2024/0306944 A1    Sep. 19, 2024

(51) Int. Cl.
*A61B 5/1172* (2016.01)
(52) U.S. Cl.
CPC .................. *A61B 5/1172* (2013.01)

(58) Field of Classification Search
CPC .......................................... G06V 40/12–1394
See application file for complete search history.

(56) References Cited

U.S. PATENT DOCUMENTS

| | | | |
|---|---|---|---|
| 9,524,415 B2* | 12/2016 | Liu | H01H 11/0062 |
| 10,726,233 B2* | 7/2020 | Kern | G09G 5/02 |
| 2020/0193115 A1 | 6/2020 | Schultz et al. | |

FOREIGN PATENT DOCUMENTS

| | | |
|---|---|---|
| CN | 109791177 A | 5/2019 |
| CN | 110503026 A | 11/2019 |
| JP | 2003-060186 A | 2/2003 |
| JP | 2005-292090 A | 10/2005 |
| JP | 2020-086749 A | 6/2020 |

OTHER PUBLICATIONS

International Search Report for PCT Application No. PCT/JP2021/010837, mailed on May 25, 2021.

* cited by examiner

*Primary Examiner* — Leon W Rhodes, Jr.
(74) *Attorney, Agent, or Firm* — Sughrue Mion, PLLC

(57) ABSTRACT

A test jig has a contact surface that is brought into contact with an imaging surface of a skin pattern input device, and a groove portion that is provided on the contact surface and connected to the outer edge of the contact surface.

12 Claims, 9 Drawing Sheets

TEST JIG, TEST DEVICE, AND TEST METHOD

This application is a National Stage Entry of PCT/JP2021/010837 filed on Mar. 17, 2021, the contents of all of which are incorporated herein by reference, in their entirety.

TECHNICAL FIELD

The present disclosure relates to a test jig, a test device, and a test method.

BACKGROUND ART

For example, Patent Document 1 discloses an imaging device that captures fingerprints through a prism. The imaging device disclosed in Patent Document 1 uses two imaging units to capture fingerprints through a prism.

PRIOR ART DOCUMENTS

Patent Documents

Patent Document 1: Japanese Unexamined Patent Application, First Publication No. 2020-86749

SUMMARY OF THE DISCLOSURE

Problems to be Solved by the Disclosure

For an imaging device that captures skin patterns, as disclosed in Patent Document 1, it is necessary to test the optical characteristics of the optical axis and angle of view of the imaging range in order to verify that the optical characteristics of the product performance are reasonable during the manufacturing process. For example, in the imaging device of Patent Document 1, the prism surface that the fingerprint contacts is the imaging range. In order to perform a stable optical test, it is necessary to use a test chart to measure optical properties rather than actual human skin.

However, the imaging device disclosed in Patent Document 1 utilizes a prism-based system that takes advantage of the difference in the refractive index between human skin (approximately 1.4) and air (approximately 1.0). Therefore, when using a test chart printed on photographic paper or film used for general optical testing, it is necessary to eliminate the air between the prism and the test chart, posing a challenge for stable optical testing.

The purpose of this disclosure is to provide a test jig, a test device, and a test method that enables stable optical tests in view of the above-mentioned issues.

Means for Solving the Problem

The test jig that is one example aspect of the present disclosure has a contact surface that is brought into contact with an imaging surface of a skin pattern input device, and a groove portion that is provided on the contact surface and connected to an outer edge of the contact surface.

The test device that is one example aspect of the present disclosure is provided with an image acquisition means that acquires an image of the contact surface captured by a skin pattern input device using the test jig that is an example aspect of the present disclosure, an optical characteristic calculation means that calculates the optical characteristics of the skin pattern input device based on the image acquired by the image acquisition means, and a determination means that determines the state of the skin pattern input device based on the optical characteristics calculated by the optical characteristic calculation means.

In the test method that is one example aspect of the present disclosure, a test jig has a contact surface that is brought into contact with an imaging surface of a skin pattern input device, and a groove portion that is provided on the contact surface and connected to the outer edge of the contact surface, the method acquiring an image of the contact surface captured by a skin pattern input device using the test jig; calculating an optical characteristic of the skin pattern input device based on the image; and determining the state of the skin pattern input device based on the optical characteristic.

EXAMPLE EMBODIMENT

Hereinbelow, each example embodiment of the present disclosure will be described using the drawings. The drawings and specific configurations used in each example embodiment should not be used to interpret the invention.

First Example Embodiment

Figure 1:
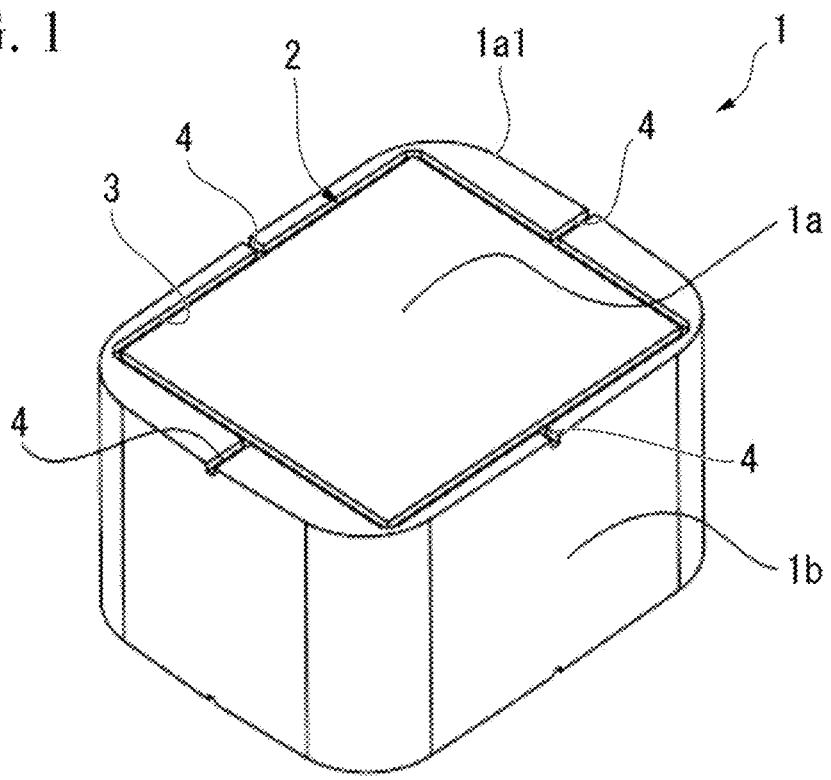
FIG. 1 is a perspective diagram of the test chart in the first example embodiment of the present disclosure.

FIG. 1 is a perspective diagram of a test chart 1 (test jig) in the first example embodiment of the present disclosure. The test chart 1 is formed in a block shape having a contact surface 1a that is brought into contact with an imaging surface 103a of a fingerprint input device 100 (skin pattern input device) to be tested (described below) and a peripheral surface 1b provided along an outer edge 1a1 of the contact surface 1a. The test chart 1 in the present example embodiment is made of silicone resin, which has a refractive index close to that of human skin (about 1.4).

Figure 2:
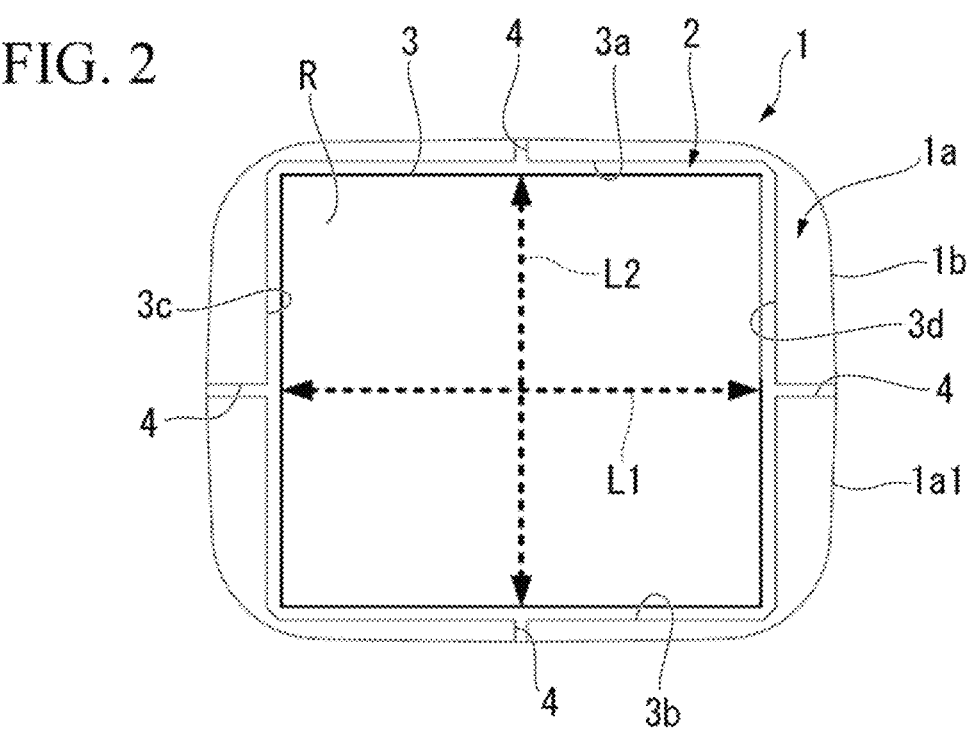
FIG. 2 is a front view of the contact surface of the test chart in the first example embodiment of the present disclosure.

FIG. 2 shows a front view of the contact surface 1a of the test chart 1. As shown in FIGS. 1 and 2, the contact surface 1a of the test chart 1 is provided with a groove portion 2. The groove portion 2 is a guideway that discharges air between the contact surface 1a and the imaging surface from the interface between the contact surface 1a and the imaging surface to the outside when the contact surface 1a is pressed against the imaging surface of the fingerprint input device 100. The groove portion 2 is used as a test pattern for testing the optical characteristics of the fingerprint input device 100. The groove portion 2 is recessed from the contact surface 1a at a certain depth dimension and has one frame portion 3 and a plurality of connection portions 4 (four in the present example embodiment).

The frame portion 3 is rectangular in shape when viewed from the normal direction of the contact surface 1a. In other words, the frame portion 3 is annular. This frame portion 3 has a pair of long sides (first long side 3a and second long side 3b) and a pair of short sides (first short side 3c and second short side 3d). One end of the first long side 3a is connected to one end of the first short side 3c, the other end of the first long side 3a is connected to one end of the second short side 3d, one end of the second long side 3b is connected to the other end of the first short side 3c, and the other end of the second long side 3b is connected to the other end of the second short side 3d. By connecting these long sides and short sides, the frame portion 3 is formed into a rectangular shape as described above. The area surrounded by the frame portion 3 is used as a central region R, which is used when testing the optical characteristics of the fingerprint input device 100. In other words, the ring-shaped frame portion 3 forms the central region R used when testing the optical characteristics of the fingerprint input device 100.

The connection portion 4 is the portion that connects the frame portion 3 to the outer edge 1a1 of the contact surface 1a. In this system, four connection portions 4 are provided. As shown in FIGS. 1 and 2, one connection portion 4 is formed in a straight line so as to connect the center of the first long side 3a with the outer edge 1a1. One connection portion 4 is formed in a straight line so as to connect the center of the second long side 3b with the outer edge 1a1. One connection portion 4 is formed in a straight line so as to connect the center of the first short side 3c with the outer edge 1a1. One connection portion 4 is formed in a straight line so as to connect the center of the second short side 3d with the outer edge 1a1. Since the peripheral surface 1b is formed along the outer edge 1a1 of the contact surface 1a as described above, each of the connection portions 4 connects the frame portion 3 and the peripheral surface 1b.

When the optical characteristics of the fingerprint input device 100 are tested using this test chart 1, the horizontal direction on the optical characteristics of the camera for natural images (described below) equipped with the fingerprint input device 100 becomes the direction along the long sides of the frame portion 3. The vertical direction on the optical characteristics of the camera for natural images becomes the direction along the short sides of the frame portion 3. For this purpose, the virtual line segment extending parallel to the long sides and centered in the longitudinal direction of the short sides is referred to as the horizontal center line L1, as shown in FIG. 2. The virtual line segment extending parallel to the short sides and centered in the longitudinal direction of the long sides is referred to as the vertical center line L2.

The groove portion 2 serves as a channel through which air flows when the contact surface 1a is pressed against the imaging surface of the fingerprint input device 100. Since the connection portion 4 of the groove portion 2 is connected to the outer edge 1a1 of the contact surface 1a (peripheral surface 1b), air flowing through the groove portion 2 is discharged to the outside of the test chart 1. Thus, the test chart 1 in the present example embodiment has a structure that allows air to easily escape to the periphery of the silicone resin surface (contact surface 1a) that contacts the imaging surface of the fingerprint input device 100. Furthermore, the groove portion 2 also serves as a pattern (guide) for testing the optical axis and angle of view in the optical test of the fingerprint input device 100. By applying pressure to this test chart 1 toward the imaging surface of the fingerprint input device 100, it is possible to eliminate the air between the imaging surface and the contact surface 1a. The contact surface 1a should have a mirror finish to prevent excess air from entering between it and the imaging surface 103a of the fingerprint input device 100.

The fact that the test chart 1 is made of a material (silicone resin) that is close to the refractive index of human skin allows for clear imaging of the contact surface 1a. On the other hand, the portion of the groove portion 2 that does not contact the imaging surface becomes an air layer. Therefore, the contrast in the area where the groove portion 2 is provided is very low. Using this, the optical axis and angle of view can be calculated from the position of the groove portion 2 in the captured image, and the optical characteristics can be tested. The test method for optical characteristics will be explained in detail in a later section.

Figure 3:
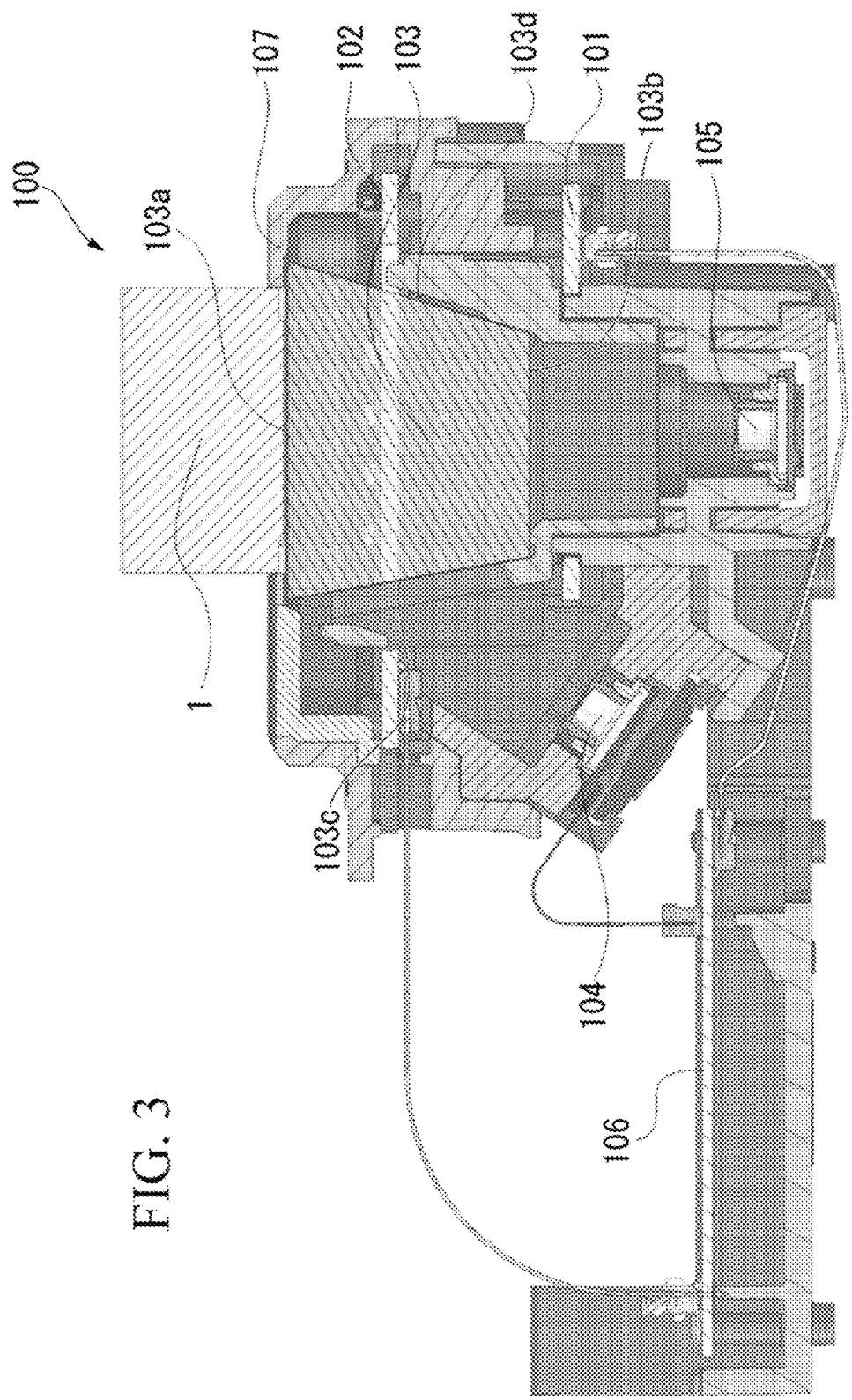
FIG. 3 is a cross-sectional view of the schematic configuration of the fingerprint input device to be tested using the test chart.

FIG. 3 shows a cross-sectional view of the schematic configuration of the fingerprint input device 100 for which testing is performed using the test chart 1. The fingerprint input device 100 is a device that captures an image of a fingerprint at the fingertip (the end of a human finger) and outputs the captured image. The target device for testing using the test chart 1 is not limited to the fingerprint input device 100. A palm print input device that images palm prints and other skin pattern input devices that image skin patterns are subject to testing. The skin pattern input device to be tested has an identical configuration, except for differences in the size of the imaging surface, and the like. For this reason, a representative description of the fingerprint input device 100 is provided here.

As shown in FIG. 3, the fingerprint input device 100 has a white light LED substrate 101, a near-infrared light LED substrate 102, a prism 103, a fingerprint imaging camera 104, a natural image imaging camera 105, and a control substrate 106.

The white light LED substrate 101 is located below the prism 103 and has a visible light LED such as a white LED (light emitting diode), which outputs white light toward the upper part of FIG. 3. White light contains visible light components with wavelengths ranging from 380 to 800 nm. White light enters the interior of the prism 103 from a facing surface 103b of the prism 103 and is irradiated toward the fingertip placed on an imaging surface 103a of the prism 103 (the contact surface 1a of the test chart 1 during a test).

The near-infrared light LED substrate 102 is provided to enclose the prism 103 from a side and has multiple near-infrared light LEDs, which output near-infrared light with a wavelength longer than that of white light. Near-infrared light includes infrared light components with wavelengths of about 800 nm to 1000 nm. A light guide 107 that guides the near-infrared light is located between the near-infrared light LED substrate 102 and the side of the imaging surface 103a of the prism 103. By being guided by the light guide 107, the near-infrared light is irradiated along the imaging surface 103a to the fingertip (contact surface 1a of the test chart 1 during testing).

The light guide 107 is positioned to surround the imaging surface 103a. The test chart 1 in this example embodiment is shaped to fit into the area enclosed by the light guide 107. In other words, the test chart 1 is formed so that the peripheral surface 1b of the test chart 1 abuts the light guide 107 when the contact surface 1a of the test chart 1 contacts the imaging surface 103a.

The prism 103 has an imaging surface 103a on which the fingertip, which is the imaging target, is placed, and an facing surface 103b that faces the imaging surface 103a. The prism 103 is a polyhedron (e.g., hexahedron) with a refractive index different from that of air and can be made of glass, crystal, or other material. The facing surface 103b may or may not be parallel to the imaging surface 103a. The surface with respect to which the fingerprint imaging camera 104 is oppositely arranged is an intersecting surface 103c, which intersects the imaging surface 103a at a predetermined angle. A surface 103d located on the opposite side of the intersecting surface 103c is coated with black paint or other color to enhance the contrast of the image. Instead of applying black paint, a black board may be affixed.

The fingerprint imaging camera 104 captures an image of the fingertip, the object, from the intersecting surface 103c side (at the time of the test, the contact surface 1a of the test chart 1). The fingerprint imaging camera 104 has an image sensor such as a CMOS (complementary metal oxide semiconductor) image sensor or CCD (charge coupled device) image sensor, converts the visible and infrared light components that are input into an image signal and outputs the image signal. In this case, the fingerprint imaging camera 104 does not have an infrared light cut filter and is highly sensitive to white light and near-infrared light.

The natural image imaging camera 105 captures an image of the object, which is the fingertip, from the facing surface 103b side (at the time of testing, the contact surface 1a of the test chart 1). The natural image imaging camera 105 has an image sensor such as a CMOS image sensor or CCD image sensor and an infrared light cut filter to convert the input visible light component into an image signal for output. In this case, the natural image imaging camera 105 has low sensitivity to near-infrared light. However, the natural image imaging camera 105 may not have an infrared light cut filter, but may use image processing, for example, to achieve the same effect as if an infrared light cut filter were provided.

The control substrate 106 is a substrate on which arithmetic circuit chips for arithmetic processing and memory chips for storage are mounted. The control substrate 106 controls the fingerprint imaging camera 104 and the natural image imaging camera 105. In other words, the control substrate 106 causes the fingerprint imaging camera 104 to capture the fingerprint (contact surface 1a of test chart 1 during testing). The control substrate 106 also causes the natural image imaging camera 105 to capture the fingerprint (contact surface 1a of the test chart 1 during testing). The control substrate 106 also controls the white light LED substrate 101 and the near-infrared light LED substrate 102.

When capturing a fingerprint with the fingerprint input device 100, the fingertip is placed on the imaging surface 103a of the prism 103. The white light output by the white light LED substrate 101 is reflected by the ridge lines and valley lines of the fingerprint and enters the prism 103. The near-infrared light output by the near-infrared light LED substrate 102 passes through the fingertip, is emitted from the ridge lines and valley lines of the fingerprint located on the imaging surface 103a, and enters the prism 103 from the imaging surface 103a.

The ridges of the fingerprint are in contact with the imaging surface 103a. Therefore, the refractive index of light incident on or reflected from the ridge line portion is almost the same as the refractive index of the prism 103 (glass and the like). Therefore, the light emitted from or reflected by the ridge line portion can be considered as light reflected by the imaging surface 103a, and is radiated almost equally in all directions within the prism 103, reaching all regions below the imaging surface 103a.

On the other hand, the valley line portion of the fingerprint is not in contact with the imaging surface 103a, and so there is an air layer between the valley line portion and the imaging surface 103a. Therefore, the outgoing light from the valley line or reflected light at the valley line enters the imaging surface 103a through the air layer. Here, the refractive index of air is 1.0. The refractive index of glass is generally around 1.5 and ranges from 1.3 to 2.0. The refractive index of water and skin is 1.3 to 1.4. Because of these differences in refractive indices, the outgoing light and reflected light from the valley line portion will have different refractive phenomena than the outgoing light and reflected light from the ridge line portion. Therefore, the outgoing light and reflected light from the valley line portion is not radiated in all directions. Since the refraction angle is smaller than the incident angle, the outgoing light from the valley line portion and the reflected light at the valley line portion will be biased towards the downward direction within the prism 103.

As described above, light from the ridge line portion radiates almost equally in all directions from the imaging surface 103a, while light from the valley line portion is radiated from the imaging surface 103a in a downward biased direction. Since the light from the valley line portion is radiated in a downward biased direction, the angle of incidence to the intersecting surface 103c is larger than that from the ridge line portion. Therefore, compared to the light from the ridge line portion, the light from the valley line portion has a larger proportion of the incident angle exceeding the critical angle, and a larger proportion of the light is totally reflected at the intersecting surface 103c. Therefore, more light from the ridge line portion than from the valley line portion reaches the fingerprint imaging camera 104, which captures the fingertip from the intersecting surface 103c side. Therefore, the image captured by the fingerprint imaging camera 104 is a high-contrast fingerprint image (hereinafter referred to as a high-contrast image) with bright ridge lines and dark valley lines.

During imaging, the fingertip is illuminated from the facing surface 103b side with white light and from the periphery of the imaging surface 103a with near-infrared light. In this case, the near-infrared light can brighten the periphery of the fingertip, which is difficult for white light to reach. Thus, the fingerprint imaging camera 104 can capture a fingerprint with the entire fingerprint properly illuminated. Therefore, according to the fingerprint input device 100, the contrast can be high throughout the fingerprint image.

On the other hand, the light from the ridge line portion and the light from the valley line portion reaches the natural image imaging camera 105, which captures the fingertip from the facing surface 103b side, in roughly equal proportions compared to the proportions reaching the fingerprint imaging camera 104. The image captured by the natural image imaging camera 105 is similar to that of a direct view of the fingertip placed on the imaging surface 103a from the facing surface 103b. The image captured by the natural image imaging camera 105 is an image with a suppressed infrared light component. Therefore, the image captured by the natural image imaging camera 105 is a natural image of the fingertip (hereinafter referred to as a natural image).

The high-contrast image captured by the fingerprint imaging camera 104 is used for fingerprint verification, for example. The fingerprint input device 100 can easily improve the accuracy of fingerprint verification, for example, because the fingerprint imaging camera 104 can capture high-contrast fingerprint images over the entire area. On the other hand, the natural image captured by the natural image imaging camera 105 is used, for example, to determine whether the fingertip is fake or real.

Next, an example of imaging the test chart 1 is described. During the manufacture of the fingerprint input device 100, a test is performed to determine whether the optical characteristics of the fingerprint input device 100 pass or fail. The test chart 1 of the present example embodiment is used for pass/fail testing of the optical characteristics performed during the manufacture of such a fingerprint input device 100. However, the test chart 1 may be used to test the fingerprint input device 100 during maintenance, and the like, not only during manufacturing.

When using the test chart 1 for testing, the orientation of the test chart 1 is made an orientation in which the contact surface 1a facing downward, and the contact surface 1a is brought into contact with the imaging surface 103a of the fingerprint input device 100. In this state, imaging of the contact surface 1a is performed. The white light output by the white light LED substrate 101 is reflected by the contact surface 1a of the test chart 1 and enters the prism 103. The near-infrared light output by the near-infrared light LED substrate 102 passes through the peripheral surface 1b of the test chart 1, is emitted from the contact surface 1a of the test chart 1, and enters the prism 103 from the imaging surface 103a.

The area of the contact surface 1a excluding the groove portion 2 (hereinafter referred to as the contact area) is in contact with the imaging surface 103a. Therefore, the refractive index of light incident from the contact area or reflected by the contact area is almost the same as the refractive index of the prism 103 (glass, etc.). Therefore, the light emitted from the contact area or reflected by the contact area can be considered the same as light reflected by the imaging surface 103a, and is radiated almost equally in all directions within the prism 103, reaching all regions below the imaging surface 103a.

On the other hand, the groove portion 2 is not in contact with the imaging surface 103a, and there is an air layer between the inner wall surface of the groove portion 2 and the imaging surface 103a. Therefore, the light emitted from the groove portion 2 or reflected by the groove portion 2 enters the imaging surface 103a through the air layer. As noted above, the refractive index of air is 1.0. The refractive index of glass is generally around 1.5 and ranges from 1.3 to 2.0. The refractive index of the test chart 1 is close to the refractive index of human skin (about 1.4). Because of these differences in the refractive index, the outgoing and reflected light from the groove portion 2 has a different refractive phenomenon than the outgoing and reflected light from the contact area. Therefore, the outgoing light and reflected light from the groove portion 2 is not radiated in all directions. Since the refraction angle is smaller than the incident angle, the outgoing light from the groove portion 2 and the reflected light at the groove portion 2 will be biased downward in the prism 103.

As described above, light from the contact are is emitted almost equally in all directions from the imaging surface 103a, while light from the groove portion 2 is biased downward from the imaging surface 103a. Since the light from the groove portion 2 is biased downward and radiated in a downward direction, the angle of incidence on the intersecting surface 103c is larger compared to the light from the contact area. Therefore, compared to the light from the contact area, the light from the groove portion 2 has a larger proportion of the incident angle exceeding the critical angle, and so a larger proportion of the light is totally reflected at the intersecting surface 103c. Therefore, more light from the contact area reaches the fingerprint imaging camera 104 from the intersecting surface 103c side than from the groove portion 2. Therefore, the image captured by the fingerprint imaging camera 104 is a high-contrast image, with the contact area bright and the groove portion 2 dark.

During imaging, the test chart 1 is illuminated from the facing surface 103b side with white light and from the periphery of the imaging surface 103a with near-infrared light. In this case, the near-infrared light can brighten the area around the outer edge 1a1 of the test chart 1, where white light is difficult to reach. Therefore, the fingerprint imaging camera 104 can image the contact surface 1A with the entire contact surface 1A properly illuminated. Accordingly, according to the fingerprint input device 100, the contrast can be high throughout the image of the contact surface 1a.

On the other hand, the light from the contact area and the light from the groove portion 2 reach the natural image imaging camera 105, which captures images of the contact surface 1a from the facing surface 103b, in roughly equal proportions compared to the proportions reaching the fingerprint imaging camera 104. The image captured by the natural image imaging camera 105 is similar to that of a direct view from the facing surface 103b of the fingertip placed on the imaging surface 103a. The image captured by the natural image imaging camera 105 is an image with a suppressed infrared light component. Therefore, the image captured by the natural image imaging camera 105 is a natural image of the contact surface 1a.

Based on the images obtained using the test chart 1, a pass/fail test of the optical characteristics of the fingerprint input device 100 is performed. Specifically, the optical characteristics of the fingerprint imaging camera 104 are tested based on the high-contrast image of the contact surface 1a captured by the fingerprint imaging camera 104 described above. The optical characteristics of the natural image imaging camera 105 are tested based on the natural image of the contact surface 1a captured by the natural image imaging camera 105 described above. The details of the test of the optical characteristics based on such images will be explained in later example embodiments.

The test chart 1 in the example embodiment as described above has the contact surface 1a that is brought into contact with the imaging surface 103a of the fingerprint input device 100. The test chart 1 has the groove portion 2 provided on the contact surface 1a and connected to the outer edge 1a1 of the contact surface 1a. Therefore, when the contact surface 1a is pressed against the imaging surface 103a of the fingerprint input device 100, air between the contact surface 1a and the imaging surface 103a flows through the groove portion 2 and is discharged outside the test chart 1. Therefore, the test chart 1 of the present example embodiment enables stable optical testing.

In the test chart 1 of the present example embodiment, the groove portion 2 has the frame portion 3 provided in an annular shape and the connection portion 4 connecting the frame portion 3 to the outer edge 1a1 of the contact surface 1a. This allows air between the contact surface 1a and the imaging surface 103a to be discharged and the shape of the frame portion 3, for example, to be used as a pattern for testing optical characteristics. The test method using the shape of the frame portion 3 will be discussed in detail in a later example embodiment.

In the test chart 1 of the present example embodiment, the connection portion 4 is provided in plurality with respect to the frame portion 3. This allows air to be discharged from the interface between the contact surface 1a and the imaging surface 103a of the fingerprint input device 100 through the respective connection portions 4. Thus, air can be discharged more efficiently and reliably.

In the test chart 1 of the present example embodiment, the test chart 1 is formed using silicone resin, which has a refractive index close to that of human skin. In other words, the contact surface 1a is formed of silicone resin. This allows clear imaging of the contact surface 1a.

Second Example Embodiment

The second example embodiment of this disclosure is described next. In the description of the present example embodiment, description of those portions similar to those in the first example embodiment mentioned above will be omitted or simplified.

Figure 4:
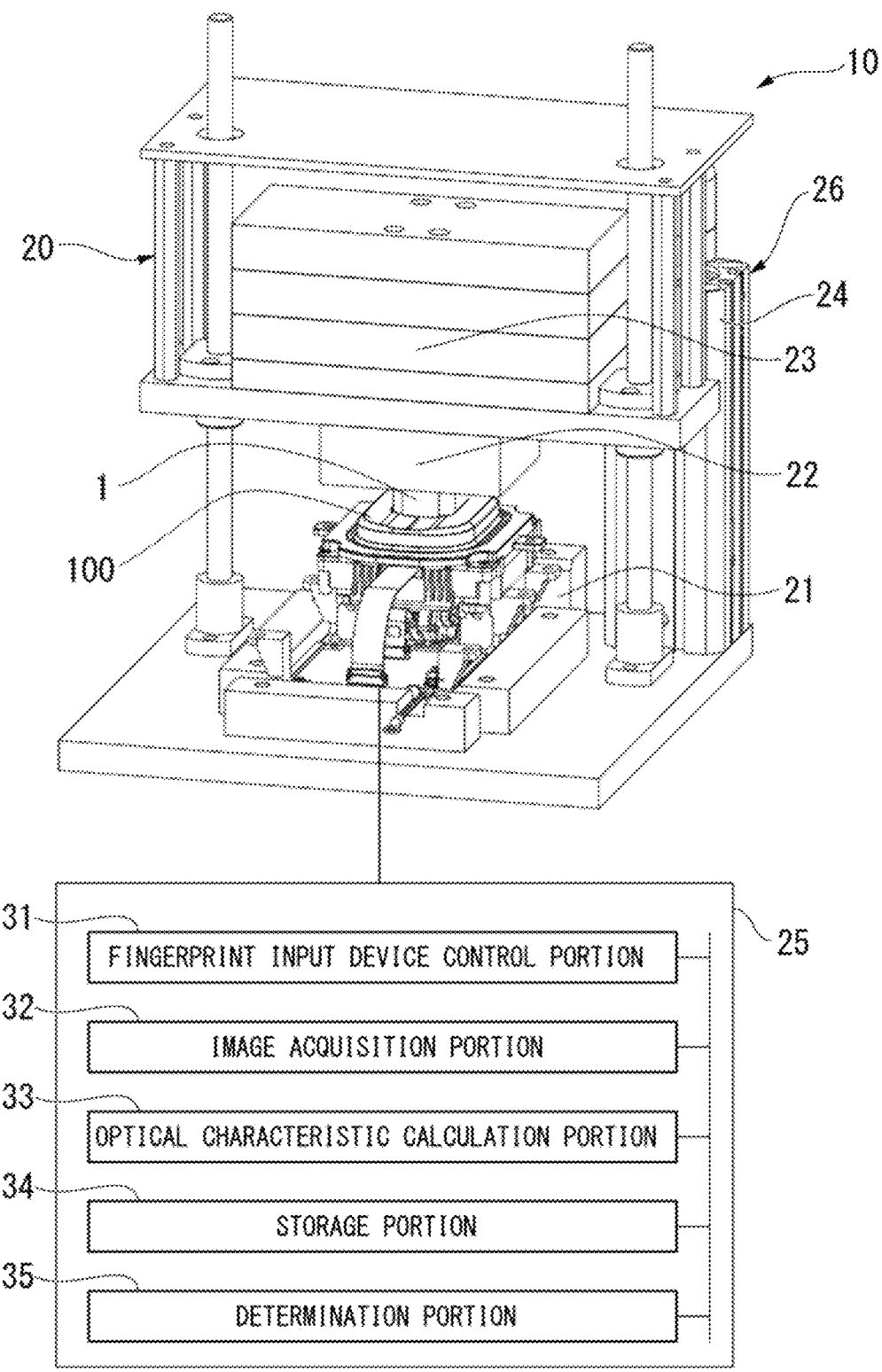
FIG. 4 is a schematic diagram of the test system of the second example embodiment of the present disclosure.

FIG. 4 shows a schematic diagram of the test system 1 of the present example embodiment. As shown in this figure, the test system 10 of the present example embodiment is equipped with the test chart 1 of the first example embodiment above and a test device 20.

The test device 20 is a device that detects the optical characteristics of the fingerprint input device 100 to be inspected and performs a pass/fail reversal to determine whether the optical characteristics have a predetermined range of performance. As shown in FIG. 4, the test device 20 is equipped with an installation stand 21 (fixing means), a pressurizing stand 22, a weight 23, an actuator 24, and a control operation portion 25.

The installation stand 21 is a stand on which the fingerprint input device 100 to be tested is installed, and fixes the fingerprint input device 100 to a test position. The pressurizing stand 22 is a stand that abuts from above the test chart 1, whose contact surface 1a is in contact with the imaging surface 103a of the fingerprint input device 100, and is supported in an elevatable manner. The weight 23 is placed on the pressurizing stand 22 and supported by the pressurizing stand 22. As shown in FIG. 4, the number of weights 23 can be changed. The actuator 24 is a device that raises and lowers the pressurizing stand 22 by extending and retracting a rod in the vertical direction under the control of the control operation portion 25, and is fixed to the installation stand 21. The actuator 24 is configured to adjust the support force of the pressurizing stand 22, and by adjusting the support force, the load acting on the test chart 1 from the pressurizing stand 22 can be adjusted.

The pressurizing stand 22, weight 23, and actuator 24 work together to press the contact surface 1a of the test chart 1 onto the imaging surface 103a of the fingerprint input device 100. In other words, the pressurizing stand 22, weight 23, and actuator 24 constitute a pressing portion 26 that presses the contact surface 1a of the test chart 1 onto the imaging surface 103a of the fingerprint input device 100. The test device 20 can also be made to consist of the control operation portion 25, without the installation stand 21, pressurizing stand 22, weight 23, and actuator 24.

The control operation portion 25, for example, consists of a computer with respective hardware such as a CPU (Central Processing Unit), ROM (Read Only Memory), RAM (Random Access Memory), and a communication module. As shown in FIG. 4, the control operation portion 25 has the following functional portions embodied in the above hardware: an actuator control portion 30, a fingerprint input device control portion 31, an image acquisition portion 32 (image acquisition means), an optical characteristic calculation portion 33 (optical characteristic calculation means), a storage portion 34, and a determination portion 35 (determination means).

The actuator control portion 30 controls the actuator 24 and causes the actuator 24 to raise and lower the pressurizing stand 22. The actuator control portion 30 controls the actuator 24 to adjust the support force of the pressurizing stand 22 and the pressing force acting on the test chart 1.

The fingerprint input device control portion 31 is connected to the fingerprint input device 100 fixed to the installation stand 21 and controls the entire fingerprint input device 100 through the control substrate 106 of the fingerprint input device 100. In other words, the fingerprint input device control portion 31 causes the fingerprint imaging camera 104 and the natural image imaging camera 105 of the fingerprint input device 100 to image the contact surface 1a of the test chart 1.

The image acquisition portion 32 acquires images of the contact surface 1a of the test chart 1 captured by the fingerprint imaging camera 104 and the natural image imaging camera 105 of the fingerprint input device 100 under the control of the fingerprint input device control portion 31. In other words, the image acquisition portion 32 acquires an image of the contact surface 1a captured by the fingerprint input device 100 using the test chart 1.

The optical characteristic calculation portion 33 calculates the optical characteristics of the fingerprint input device 100 based on the image acquired by the image acquisition portion 32. The optical characteristic calculation portion 33 calculates the optical axes of the fingerprint imaging camera 104 and the natural image imaging camera 105 and the angle of view of the fingerprint imaging camera 104 and the natural image imaging camera 105 as the optical characteristics of the fingerprint input device 100.

When calculating the optical axis, the optical characteristic calculation portion 33 first defines the horizontal center line L1 (the first reference line along the contact surface 1a) and the vertical center line L2 (the second reference line along the contact surface 1a and orthogonal to the first reference line) described above, based on the location of the groove portion 2 included in the image. The optical characteristic calculation portion 33 then calculates the optical axis position based on the intersection position of the horizontal center line L1 and the vertical center line L2.

More specifically, when calculating the optical axis of the fingerprint imaging camera 104, the optical characteristic calculation portion 33 first defines the horizontal center line L1 and the vertical center line L2 based on the position of the groove portion 2 included in the image captured by the fingerprint imaging camera 104. The optical characteristic calculation portion 33 then calculates the optical axis position of the fingerprint imaging camera 104 based on the intersection position of the horizontal center line L1 and the vertical center line L2.

When calculating the optical axis of the natural image imaging camera 105, the optical characteristic calculation portion 33 first defines the horizontal center line L1 and the vertical center line L2 based on the position of the groove portion 2 included in the image captured by the natural image imaging camera 105. The optical characteristic calculation portion 33 then calculates the optical axis position of the natural image imaging camera 105 based on the intersection position of the horizontal center line L1 and the vertical center line L2.

When calculating the angle of view, the optical characteristic calculation portion 33 calculates the angle of view of the fingerprint imaging camera 104 and the natural image imaging camera 105 based on the length dimensions of the horizontal center line L1 and the vertical center line L2. More specifically, when calculating the angle of view of the fingerprint imaging camera 104, the optical characteristic calculation portion 33 determines the length dimension of the horizontal center line L1 and the length dimension of the vertical center line L2 from the image captured by the fingerprint imaging camera 104, and calculates the angle of view of the fingerprint imaging camera 104 from these length dimensions. When calculating the angle of view of the natural image imaging camera 105, the optical characteristic calculation portion 33 determines the length dimension of the horizontal center line L1 and the length dimension of the vertical center line L2 from the image captured by the natural image imaging camera 105, and calculates the angle of view of the natural image imaging camera 105 from these length dimensions.

The storage portion 34 stores various pieces of data, for example, determination reference values for determining the pass/fail of optical characteristics in the determination portion 35. In the present example embodiment, the design value of the optical axis position of the fingerprint imaging camera 104, the design value of the angle of view of the fingerprint imaging camera 104, the design value of the optical axis position of the natural image imaging camera 105, and the design value of the angle of view of the natural image imaging camera 105 are stored as the determination reference values.

The determination portion 35 determines the state of the fingerprint input device 100 based on the above-mentioned optical characteristics calculated by the optical characteristic calculation portion 33. The state of the fingerprint input device 100 here indicates whether the various optical characteristics calculated by the optical characteristic calculation portion 33 are within the predetermined range for the design values of the various optical characteristics stored in the storage portion 34. Note that if the various optical characteristics calculated by the optical characteristic calculation portion 33 are within the predetermined range for the design values of the various optical characteristics stored in the storage portion 34, a determination of normality is made. On the other hand, if the various optical characteristics calculated by the optical characteristic calculation portion 33 do not fall within the predetermined range for the design values of the various optical characteristics stored in the storage portion 34, a determination of abnormality is made.

Figure 5:
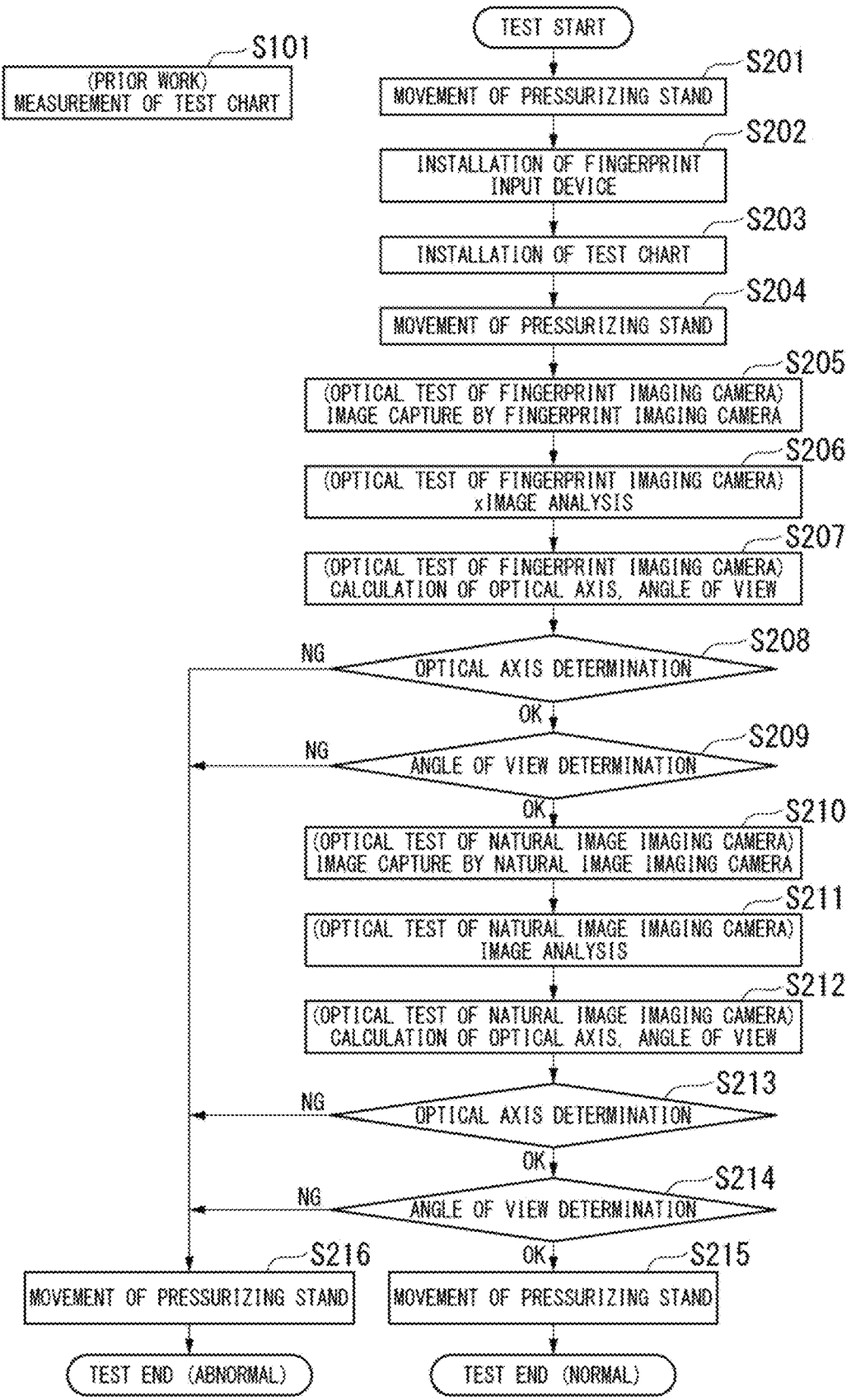
FIG. 5 is a flowchart for describing the test method of the optical characteristics of a fingerprint input device using the test chart and test device in the second example embodiment of the present disclosure.

The method of testing the optical characteristics of the fingerprint input device 100 using the test chart 1 and the test device 20 shall be described with reference to the flowchart in FIG. 5.

As a preliminary task, dimensional measurements of the horizontal center line L1 and the vertical center line L2 of the test chart 1 actually used in the test are performed (Step S101). The dimensions measured in Step S101 are used when calculating the optical axis and angle of view in Step S207 and Step S212 described below in the test of the optical characteristics of the fingerprint input device 100. The measurement in Step S101 does not need to be performed for every test of the fingerprint input device 100. Since the purpose is to reflect the dimensional individual differences of the test chart 1, this is performed for each individual test chart 1 that is actually used to inspect the fingerprint input device 100.

After the test starts, to install the fingerprint input device 100, which is the device to be tested, in the test device 20, the actuator 24 is operated to raise the pressurizing stand 22 and the weight 23 for adjusting the pressure to a position where the fingerprint input device 100 can be installed (Step S201). Here, the actuator 24 is controlled by the actuator control portion 30 of the control operation portion 25.

After the pressurizing stand 22 and the weight 23 for adjusting the pressure are raised, the fingerprint input device 100 is installed in alignment with the test position on the installation stand 21 (Step S202). After the fingerprint input device 100 is installed, the test chart 1 is placed in contact with the light guide 107 and prism 103, and the contact surface 1a is in contact with the imaging surface 103a (Step S203). The installation of the fingerprint input device 100 and the test chart 1 is performed by an operator or a work robot.

After the test chart 1 is installed, the actuator 24 is operated to move the pressurizing stand 22 and the weight 23 in the direction in which the test chart 1 is pressed against the imaging surface 103a of the fingerprint input device 100 (downward in the present example embodiment) (Step S204). The amount of pressure (pressing force) can be adjusted by the dead weight of the weight 23 for pressure adjustment. The amount of pressure (pressing force) can be further adjusted by adjusting the support force of the weight 23 (pressurizing stand 22) of the actuator 24. In the present example embodiment, as an example, the amount of pressure (pressing force) is adjusted to be about 10 N. Here, the actuator 24 is controlled by the actuator control portion 30 of the control operation portion 25.

By the movement of the pressurizing stand 22 in Step S204, the test chart 1 is pressed toward the imaging surface 103a of the fingerprint input device 100. At this time, the groove portion 2 of the test chart 1 allows the air layer between the contact surface 1a of the test chart 1 and the imaging surface 103a of the fingerprint input device 100 to escape. This prepares the test chart 1 for imaging by the fingerprint imaging camera 104.

After moving the pressurizing stand 22 in Step S204, the fingerprint imaging camera 104 is optically tested (steps S205 to S209). First, the fingerprint input device control portion 31 of the control operation portion 25 outputs a command to the control substrate 106 of the fingerprint input device 100. The control substrate 106 controls the LEDs on the near-infrared light LED substrate 102 to emit near-infrared light under the control of the fingerprint input device control portion 31. This command to the control substrate 106 does not necessarily have to be output by the control operation portion 25. For example, the operator may directly operate the control substrate 106 of the fingerprint input device 100.

When near-infrared light is emitted from the near-infrared light LED substrate 102, the fingerprint imaging camera 104 is used to capture an image of the test chart 1 (Step S205). The near-infrared light, which serves as the light source, is guided by the light guide 107 and irradiated onto the peripheral surface 1b of the test chart 1. A portion of the near-infrared light entering the test chart 1 is irradiated onto the imaging surface 103a of the prism 103.

The portion of the contact surface 1a of the test chart 1 other than the groove portion 2 (contact area) makes contact with the prism 103 without air. Since the refractive indices of silicone resin (about 1.4) and an optical glass prism (about 1.5) are almost equal, the near-infrared light travels almost straight at the contact area. Therefore, the fingerprint imaging camera 104 can capture a high-contrast image of the contact area.

On the other hand, the portion of the groove portion 2 within the contact surface 1a of the test chart 1 contacts the prism 103 through air. Due to the difference between the refractive index of silicone resin (about 1.4) and that of air (about 1.0), the near-infrared light cannot travel straight and is diffusely reflected at the contact surface between the contact surface 1a and the air. Therefore, the fingerprint imaging camera 104 captures the groove portion 2 as a low-contrast image.

When the contact surface 1a of the test chart 1 is captured by the fingerprint imaging camera 104 in this manner, the data of the image is output from the fingerprint imaging camera 104. The image acquisition portion 32 of the control operation portion 25 acquires the image of the contact surface 1a of the test chart 1 captured by the fingerprint imaging camera 104 by acquiring the data of the image output from the fingerprint imaging camera 104.

Figure 6:
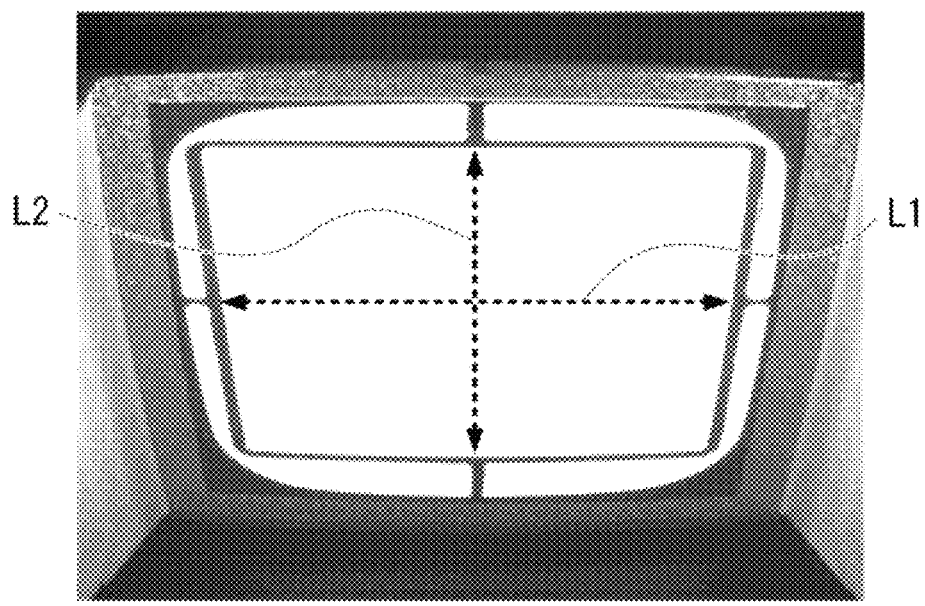
FIG. 6 is a photograph of an image captured by a fingerprint imaging camera.

Once the image of the fingerprint imaging camera 104 is obtained, image analysis is performed to obtain the information necessary to calculate the optical axis and angle of view of the fingerprint imaging camera 104 (Step S206). This image analysis shall be explained using an actual image captured by the fingerprint imaging camera 104. FIG. 6 is a photograph of an image captured by the fingerprint imaging camera 104. However, the dashed arrows, drawn lines, and signs in FIG. 6 are added for illustrative purposes and are not included in the actual image. As an image analysis, the central region R surrounded by the frame portion 3 of the groove portion 2 is extracted from the image captured by the fingerprint imaging camera 104. Next, the number of pixels of the horizontal center line L1 and the vertical center line L2 of the extracted central region R are measured.

The optical axis and angle of view of the fingerprint imaging camera 104 are then calculated from the obtained values and the design values of the fingerprint input device 100 stored in the storage portion 34 (Step S207). The optical axis position of the fingerprint imaging camera 104 is calculated from the difference between the intersection of the horizontal center line L1 and vertical center line L2 obtained by image analysis and the optical axis design value of the fingerprint input device 100. The angle of view of the fingerprint imaging camera 104 is calculated with a value obtained by finding, from the design values of the imaging surface 103a of the fingerprint input device 100, the actual dimensions per pixel to calculate the actual dimensions of the horizontal center line L1 and the vertical center line L2, and the design value of the distance from the principal point of the fingerprint imaging camera 104 of the fingerprint input device 100 to the imaging surface 103a.

The image analysis in Step S206 and the calculation of the optical axis and angle of view in Step S207 are performed by the optical characteristic calculation portion 33 of the control operation portion 25. In other words, the optical characteristic calculation portion 33 calculates the optical axis and angle of view of the fingerprint imaging camera 104 as optical characteristics based on the image captured by the fingerprint imaging camera 104 that the image acquisition portion 32 acquired in Step S205.

Next, an optical axis determination is performed based on whether the optical axis position of the fingerprint imaging camera 104 obtained in the calculation is within the design tolerance (Step S208). Here, the determination portion 35 of the control operation portion 25 compares the optical axis position calculated in Step S207 with the design value stored in the storage portion 34. If the calculated optical axis position is at a position that does not exceed the tolerance range relative to the design value, the optical axis position is determined to be within the design tolerance range. On the other hand, if the calculated optical axis position is outside the tolerance range relative to the design value, the optical axis position is determined to be outside the design tolerance range. If the optical axis position of the fingerprint imaging camera 104 obtained by the calculation is outside the design tolerance range, it is determined as a manufacturing defect (abnormality), the pressurizing stand 22 is moved (Step S216) so that the fingerprint input device 100 can be removed from the test device 20, and the test is completed.

If the optical axis position of the fingerprint imaging camera 104 obtained by the calculation is within the design tolerance range, the angle of view determination is performed to determine whether the angle of view of the fingerprint imaging camera 104 obtained by the calculation is within the design tolerance range (Step S209). Here, the determination portion 35 of the control operation portion 25 compares the angle of view calculated in Step S207 with the design value stored in the storage portion 34. If the calculated angle of view does not exceed the tolerance range relative to the design value, the angle of view is determined to be within the design tolerance range. On the other hand, if the calculated angle of view exceeds the tolerance range relative to the design value, the angle of view is determined to be outside the design tolerance range. If the angle of view of the fingerprint imaging camera 104 obtained by the calculation is outside the design tolerance range, it is determined as a manufacturing defect (abnormality), the pressurizing stand 22 is moved (Step S216) so that the fingerprint input device 100 can be removed from the test device 20, and the test is completed.

If the angle of view of the fingerprint imaging camera 104 obtained by the calculation is within the design tolerance, the optical test of the natural image imaging camera 105 is performed next (steps S210 to S214). First, the fingerprint input device control portion 31 of the control operation portion 25 outputs a command to the control substrate 106 of the fingerprint input device 100. The control substrate 106 controls the LEDs on the white light LED substrate 101 to emit white light under the control of the fingerprint input device control portion 31. This command to the control substrate 106 does not necessarily have to be output by the control operation portion 25. For example, the operator may directly operate the control substrate 106 of the fingerprint input device 100.

When the white light is emitted from the white light LED substrate 101, the test chart 1 is captured by the natural image imaging camera 105 (Step S210). The white light, which serves as the light source, enters the interior of the prism 103 from the facing surface 103b of the prism 103 and is irradiated onto the imaging surface 103a of the prism 103.

When the contact surface 1a of the test chart 1 is captured by the natural image imaging camera 105, the data of the image is output from the natural image imaging camera 105. The image acquisition portion 32 of the control operation portion 25 acquires the image of the contact surface 1a of the test chart 1 captured by the natural image imaging camera 105 by acquiring the data of the image output from the natural image imaging camera 105.

Figure 7:
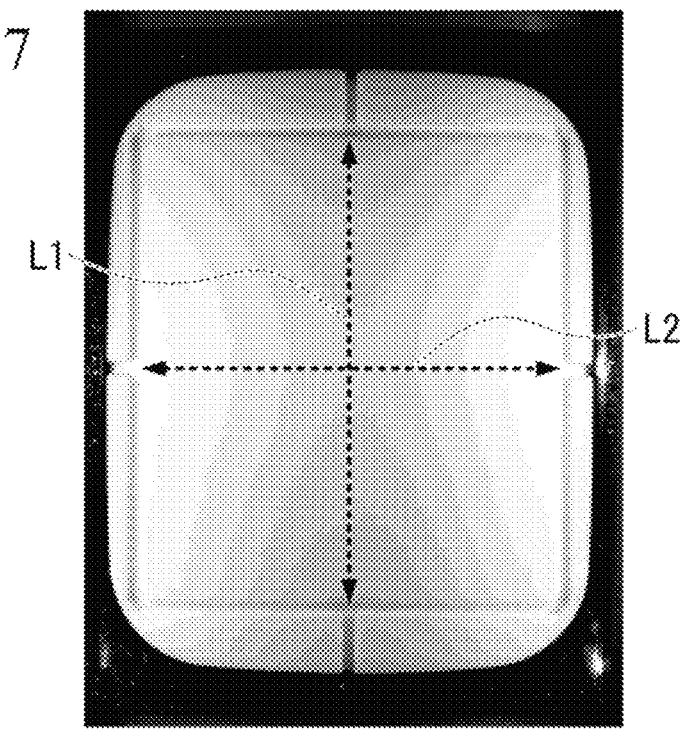
FIG. 7 is a photograph of an image captured by a natural image imaging camera.

Once the image of the natural image imaging camera 105 is obtained, image analysis is performed to obtain the information necessary to calculate the optical axis and angle of view of the natural image imaging camera 105 (Step S211). This image analysis shall be explained using an actual image captured by the natural image imaging camera 105. FIG. 7 is a photograph of an image captured by the natural image imaging camera 105. However, the dashed arrows, drawn lines, and signs in FIG. 7 are added for illustrative purposes and are not included in the actual image. The image in FIG. 7 is the actual image of the natural image imaging camera 105 rotated 90 degrees in a clockwise direction, and as the optical characteristic directions of the natural image imaging camera 105, the horizontal center line L1 in FIG. 7 is the horizontal direction and the vertical center line L2 in FIG. 7 is the vertical direction. As the image analysis, the central region R surrounded by the frame portion 3 of the groove portion 2 is extracted from the image captured by the natural image imaging camera 105. Next, the number of pixels of the horizontal center line L1 and the vertical center line L2 of the extracted central region R are measured.

The optical axis and angle of view of the natural image imaging camera 105 are then calculated from the obtained values and the design values of the fingerprint input device 100 stored in the storage portion 34 (Step S212). The optical axis position of the natural image imaging camera 105 is calculated from the difference between the intersection of the horizontal center line L1 and the vertical center line L2 obtained by image analysis and the optical axis design value of the fingerprint input device 100. The angle of view of the natural image imaging camera 105 is calculated with a value obtained by finding, from the design values of the imaging surface 103a of the fingerprint input device 100, the actual dimensions per pixel to calculate the actual dimensions of the horizontal center line L1 and the vertical center line L2, and the design value of the distance from the principal point of the natural image imaging camera 105 of the fingerprint input device 100 to the imaging surface 103a.

The image analysis in Step S211 and the calculation of the optical axis and angle of view in Step S212 are performed by the optical characteristic calculation portion 33 of the control operation portion 25. In other words, the optical characteristic calculation portion 33 calculates the optical axis and angle of view of the natural image imaging camera 105 as optical characteristics based on the image captured by the natural image imaging camera 105 that the image acquisition portion 32 acquired in Step S210.

Next, an optical axis determination is performed based on whether the optical axis position of the natural image imaging camera 105 obtained in the calculation is within the design tolerance (Step S213). Here, the determination portion 35 of the control operation portion 25 compares the optical axis position calculated in Step S212 with the design value stored in the storage portion 34. If the calculated optical axis position is at a position that does not exceed the tolerance range relative to the design value, the optical axis position is determined to be within the design tolerance range. On the other hand, if the calculated optical axis position is outside the tolerance range relative to the design value, the optical axis position is determined to be outside the design tolerance range. If the optical axis position of the natural image imaging camera 105 obtained by the calculation is outside the design tolerance range, it is determined as a manufacturing defect (abnormality), the pressurizing stand 22 is moved (Step S216) so that the fingerprint input device 100 can be removed from the test device 20, and the test is completed.

If the optical axis position of the natural image imaging camera 105 acquired by the calculation is within the design tolerance range, the angle of view determination is performed to determine whether the angle of view of the natural image imaging camera 105 acquired by the calculation is within the design tolerance range (Step S214). Here, the determination portion 35 of the control operation portion 25 compares the angle of view calculated in Step S212 with the design value stored in the storage portion 34. If the calculated angle of view does not exceed the tolerance range relative to the design value, the angle of view is determined to be within the design tolerance range. On the other hand, if the calculated angle of view exceeds the tolerance range relative to the design value, the angle of view is determined to be outside the design tolerance range. If the angle of view of the natural image imaging camera 105 obtained by the calculation is outside the design tolerance range, it is determined as a manufacturing defect (abnormality), the pressurizing stand 22 is moved (Step S216) so that the fingerprint input device 100 can be removed from the test device 20, and the test is completed.

If the angle of view of the natural image imaging camera 105 obtained by the calculation is within the design tolerance range, the pressurizing stand 22 is moved so that the fingerprint input device 100 can be removed from the test device 20 (Step S215), it is determined that there are no manufacturing abnormalities related to the optical characteristics of the optical axis and angle of view for the fingerprint imaging camera 104 and the natural image imaging camera 105, and the test is completed.

The test device 20 in the present example embodiment as described above is provided with the image acquisition portion 32 that acquires an image of the contact surface 1a captured by the fingerprint input device 100 using the test chart 1. The test device 20 is also equipped with an optical characteristic calculation portion 33 that calculates the optical characteristics of the fingerprint input device 100 based on the images acquired by the image acquisition portion 32. Furthermore, the test device 20 is equipped with the determination portion 35 that determines the state of the fingerprint input device 100 based on the optical characteristics calculated by the optical characteristic calculation portion 33. As explained in the first example embodiment above, according to the test chart 1, air between the contact surface 1a and the imaging surface 103a flows through the groove portion 2 to be discharged to the outside. Therefore, according to the test device 20, a stable optical test is possible.

In the test device 20 of the present example embodiment, the optical characteristic calculation portion 33 sets the horizontal center line L1 along the contact surface 1a and the vertical center line L2 along the contact surface 1a and orthogonal to the horizontal center line L1, based on the position of the groove portion 2 included in the image. Moreover, the optical characteristic calculation portion 33 calculates the optical axis position of the fingerprint input device 100 (the fingerprint imaging camera 104 and the natural image imaging camera 105) based on the intersection position of the horizontal center line L1 and the vertical center line L2, as an optical characteristic. Therefore, according to the test device 20 of the present example embodiment, it is possible to calculate the optical axis position by simple image processing.

In the test device 20 of the present example embodiment, the optical characteristic calculation portion 33 calculates the angle of view of the fingerprint input device 100 (fingerprint imaging camera 104 and natural image imaging camera 105) based on the length dimensions of the horizontal center line L1 and the vertical center line L2, as an optical characteristic. Therefore, according to this test device 20 of the present example embodiment, it is possible to calculate the angle of view with simple image processing.

The test device 20 of the present example embodiment is equipped with an installation stand 21 that fixes the fingerprint input device 100 and a pressing portion 26 that presses the contact surface 1a of the test chart 1 onto the imaging surface 103a of the fingerprint input device 100. Therefore, according to the test device 20, it is possible to reliably discharge air from the contact area between the imaging surface 103a of the fingerprint input device 100 and the contact surface 1a of the test chart 1.

In the test device 20 of the present example embodiment, the pressing portion 26 is provided with the pressurizing stand 22 that is in contact with the test chart 1 from above, the weight 23 supported by the pressurizing stand 22, and the actuator 24 that supports the pressurizing stand 22 in a vertically adjustable manner. This allows the pressurizing stand 22 to be easily raised and lowered using the power of the actuator 24. The amount of pressure (pressing force) on the test chart 1 can be easily adjusted by adjusting the support force of the pressurizing stand 22 by the actuator 24.

According to the test method in the present example embodiment, the test chart 1 is used. The test chart 1 has a contact surface 1a that is brought into contact with the imaging surface 103a of the fingerprint input device 100, and a groove portion 2 that is provided on the contact surface 1a and connected to the outer edge 1a1 of the contact surface 1a. In the test method of the present example embodiment, the test chart 1 is used to acquire an image of the contact surface 1a captured by the fingerprint input device 100. The optical characteristic of the fingerprint input device 100 is calculated based on the acquired image, and the state of the fingerprint input device 100 is determined based on the calculated optical characteristic. As explained in the first example embodiment above, according to the test chart 1, air between the contact surface 1a and the imaging surface 103a flows through the groove portion 2 to be discharged to the outside. Therefore, this test method of the present example embodiment enables a stable optical test.

Third Example Embodiment

Figure 8:
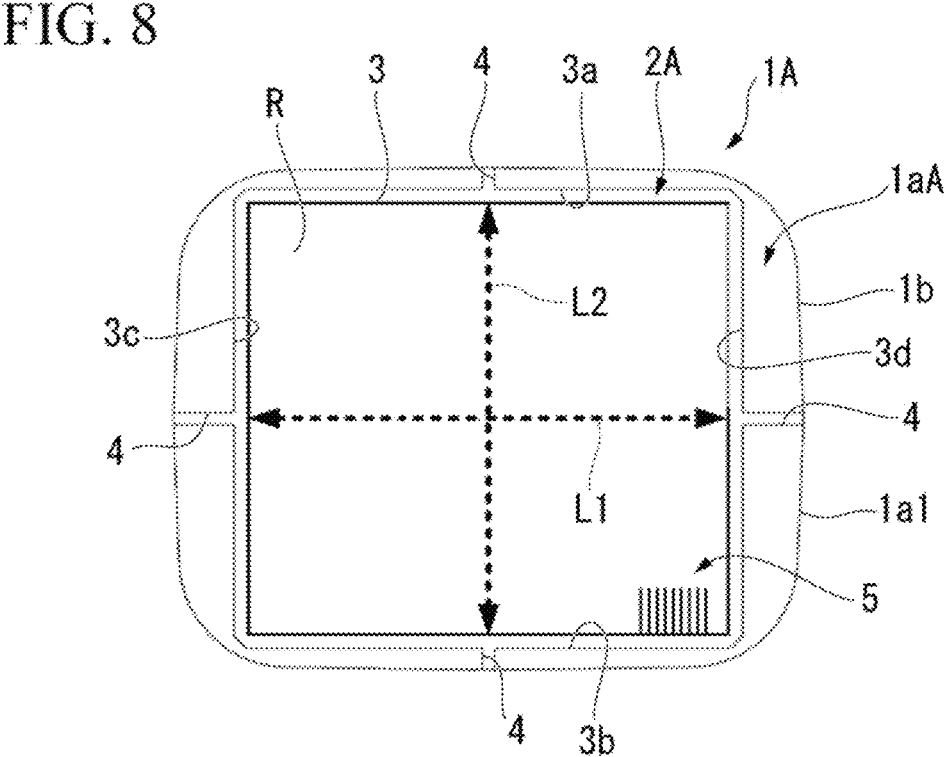
FIG. 8 is a front view of the contact surface of the test chart of the third example embodiment of the present disclosure.

Next, the third example embodiment of the present disclosure is described referring to FIG. 8. In the description of the present example embodiment, description of those portions similar to those in the first example embodiment mentioned above will be omitted or simplified.

FIG. 8 is a front view of a contact surface 1aA of a test chart 1A of the present example embodiment. As shown in this diagram, a groove portion 2A has a resolving power test portion 5 formed in a pattern that enables a resolving power test, in addition to the frame portion 3 and the connection portion 4 described above. The resolving power test portion 5 is an area for testing resolving power, which is one of the optical characteristics of the fingerprint input device 100. The resolving power test portion 5 is formed by a plurality of parallel line grooves with a pitch that can be separated and reproduced if the fingerprint input device 100 performs as designed.

In the present example embodiment, the resolving power test portion 5 is located in the central region R surrounded by the frame portion 3. However, the resolving power test portion 5 may be placed outside the central region R enclosed by the frame portion 3. The line grooves forming the resolving power test portion 5 are straight grooves, each of which has a smaller width dimension than the frame portion 3 and the connection portion 4. These line grooves are connected at one end of each to the frame portion 3, as shown in FIG. 8. Each of the line grooves forming the resolving power test portion 5 is connected to the frame portion 3, so that each of the wire grooves, as well as the frame portion 3 and the connection portion 4, can be used as a channel for discharging air outside the contact surface 1aA.

In the present example embodiment, one resolving power test portion 5 is provided. However, multiple resolving power test portions 5 may be provided. In such a case, it is possible to determine the resolving power of the fingerprint input device 100 in levels by changing the pitch of the line grooves that form each resolving power test portion 5.

Thus, in this test chart 1A, the groove portion 2A has the resolving power test portion 5 formed in a pattern enabling testing of the resolving power. By testing the optical characteristics of the fingerprint input device 100 using the test chart 1A, it is possible to determine the resolving power of the fingerprint input device 100. For example, if the shape of the resolving power test portion 5 included in the image captured by the fingerprint input device 100 is a shape capable of reproducing the respective line grooves, it is possible to determine that the resolving power of the fingerprint input device 100 is normal and meets the design value.

Fourth Example Embodiment

The fourth example embodiment of the present disclosure is described next with reference to FIGS. 9 and 10. In the description of the present example embodiment, description of those portions similar to those in the second example embodiment mentioned above will be omitted or simplified.

Figure 9:
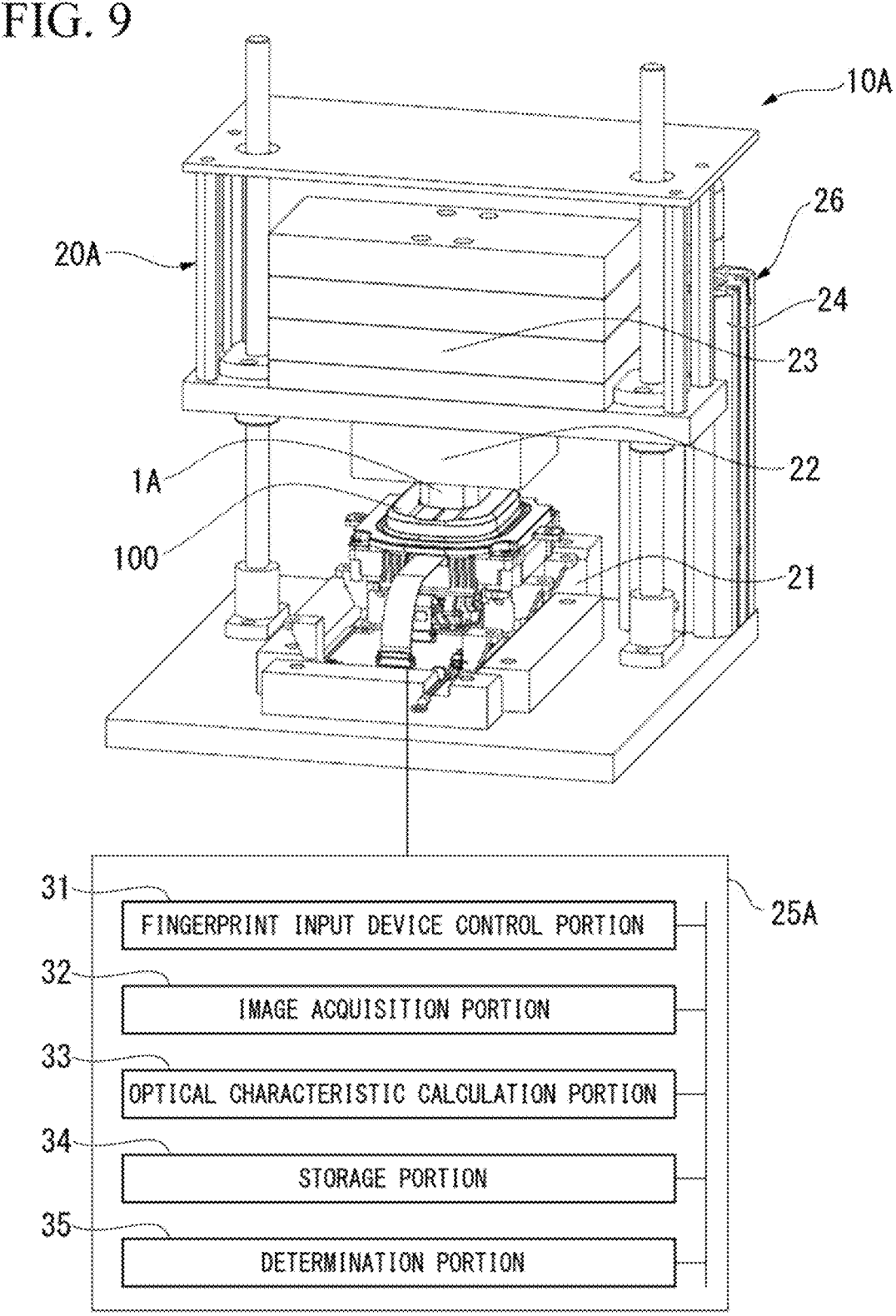
FIG. 9 is a schematic diagram of the test system of the fourth example embodiment of the present disclosure.

FIG. 9 is a schematic diagram of a test system 10A of the present example embodiment. As shown in this diagram, the test system 10A of the present example embodiment is provided with the test chart 1A of the above second example embodiment, and a test device 20A.

In a control operation portion 25A of the test device 20A, the optical characteristic calculation portion 33 calculates the resolving power of the fingerprint input device 100, which is one of the optical characteristics, in addition to the optical axis and angle of view described above. When calculating the resolving power, the optical characteristic calculation portion 33 first extracts the resolving power test portion 5 included in the image. The optical characteristic calculation portion 33 quantifies the reproducibility and roughness of the shape of the extracted resolving power test portion 5 from the image, and calculates it as the resolving power.

More specifically, when calculating the resolving power of the fingerprint imaging camera 104, the optical characteristic calculation portion 33 first extracts the resolving power test portion 5 included in the image captured by the fingerprint imaging camera 104. The optical characteristic calculation portion 33 then quantifies the reproducibility and roughness of the shape of the resolving power test portion 5 extracted from the image captured by the fingerprint imaging camera 104 and calculates it as the resolving power.

When calculating the resolving power of the natural image imaging camera 105, the optical characteristic calculation portion 33 first extracts the resolving power test portion 5 included in the image captured by the natural image imaging camera 105. The optical characteristic calculation portion 33 then quantifies the reproducibility and roughness of the shape of the resolving power test portion 5 extracted from the image captured by the natural image imaging camera 105 and calculates it as the resolving power.

As determination reference values for the determination portion 35 to determine the normality or abnormality of the optical characteristics, the storage portion 34 stores the design value of the resolving power of the fingerprint imaging camera 104 and the design value of the resolving power of the natural image imaging camera 105, in addition to the design value of the optical axis position of the fingerprint imaging camera 104, the design value of the angle of view of the fingerprint imaging camera 104, the design value of the optical axis position of the natural image imaging camera 105, and the design value of the angle of view of the natural image imaging camera 105.

The determination portion 35 determines whether the optical axis and angle of view are normal or abnormal, and also determines whether the resolving power is normal or abnormal. Specifically, the determination portion 35 determines whether the resolving power of the fingerprint imaging camera 104 is normal or abnormal. In addition, the determination portion 35 determines whether the resolving power of the natural image imaging camera 105 is normal or abnormal.

Figure 10:
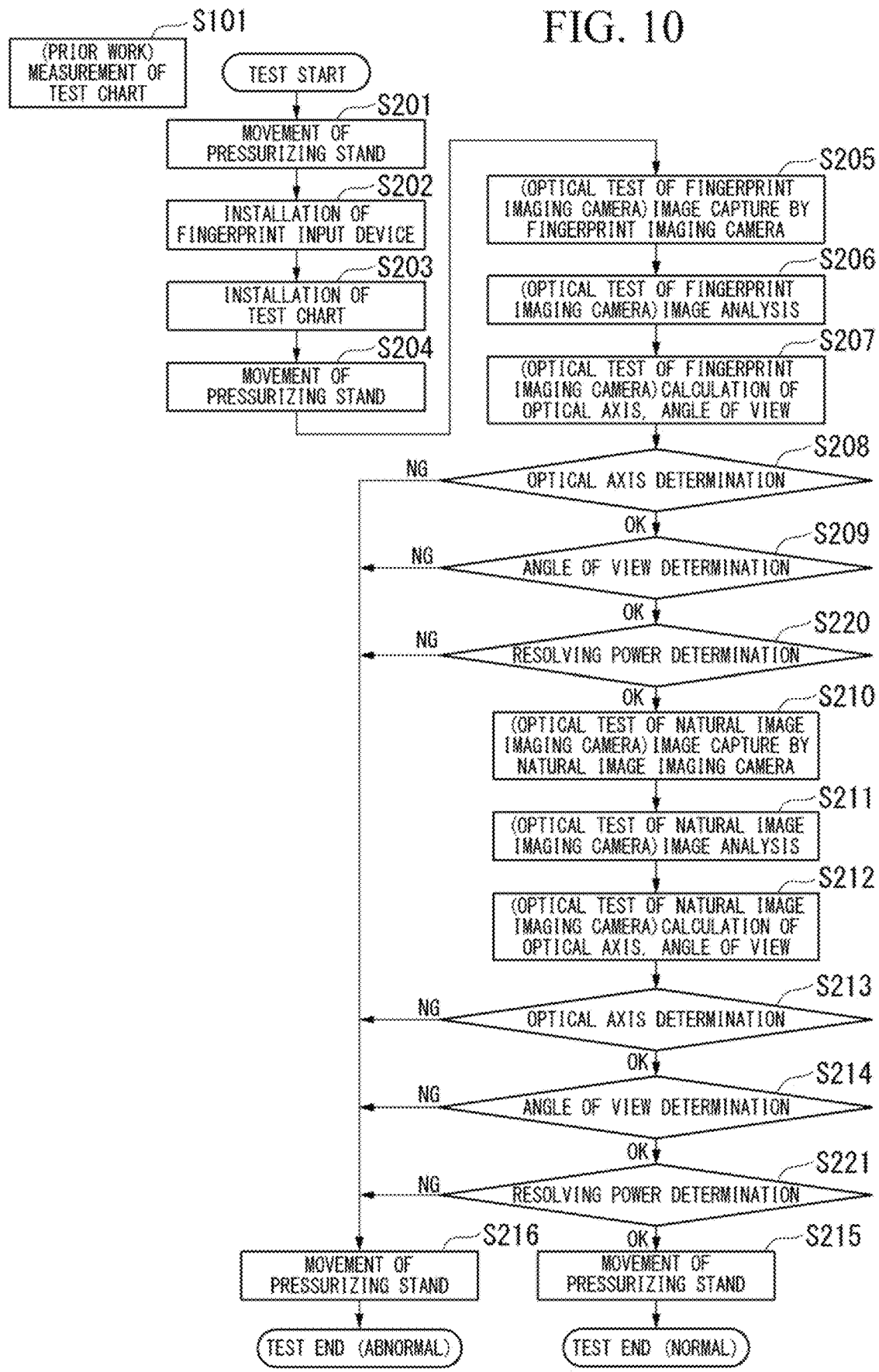
FIG. 10 is a flowchart for describing the method of testing the optical characteristics of a fingerprint input device using a test chart and test device in the fourth example embodiment of the present disclosure.

FIG. 10 is a flowchart showing the test method for the optical characteristics of the fingerprint input device 100 using the test chart 1A and the test device 20A.

In the present example embodiment, in the image analysis of Step S206, the optical characteristic calculation portion 33 extracts the resolving power test portion 5 from the image captured by the fingerprint imaging camera 104, in addition to the central region R. Then, in Step S207, the optical characteristic calculation portion 33 calculates the resolving power in addition to calculating the optical axis and angle of view.

If the angle of view of the fingerprint imaging camera 104 is within the design tolerance in Step S209 of the present example embodiment, before performing the optical test of the natural image imaging camera 105, a resolving power determination is performed depending on whether the resolving power of the fingerprint imaging camera 104 obtained by the calculation in Step S207 is within the design tolerance (Step S220). Here, the determination portion 35 of the control operation portion 25A compares the resolving power calculated in Step S207 with the design value stored in the storage portion 34. If the calculated resolving power does not exceed the tolerance range for the design value, the resolving power is determined to be within the design tolerance range. On the other hand, if the calculated resolving power exceeds the tolerance range for the design value, the resolving power is determined to be outside the design tolerance range. If the resolving power of the fingerprint imaging camera 104 obtained by the calculation is outside the design tolerance range, it is determined as a manufacturing defect (abnormality), the pressurizing stand 22 is moved (Step S216) so that the fingerprint input device 100 can be removed from the test device 20A, and the test is completed. If the resolution of the fingerprint imaging camera 104 obtained by the calculation is within the design tolerance, the optical test of the natural image imaging camera 105 is performed next.

In the image analysis of Step S212 of the present example embodiment, the optical characteristic calculation portion 33 extracts the resolving power test portion 5 in addition to the central region R from the image captured by the natural image imaging camera 105. Then, in Step S212, the optical characteristic calculation portion 33 calculates the resolving power in addition to calculating the optical axis and angle of view.

If the angle of view of the natural image imaging camera 105 is within the design tolerance range in Step S214 of the present example embodiment, before moving the pressurizing stand 22 (Step S215), a resolution determination is made depending on whether the resolving power of the natural image imaging camera 105 obtained by the calculation in Step S212 is within the design tolerance range (Step S221). Here, the determination portion 35 of the control operation portion 25A compares the resolving power calculated in Step S212 with the design value stored in the storage portion 34. If the calculated resolving power does not exceed the tolerance range for the design value, the resolving power is determined to be within the design tolerance range. On the other hand, if the calculated resolving power exceeds the tolerance range for the design value, the resolving power is determined to be outside the design tolerance range. If the resolving power of the natural image imaging camera 105 obtained by the calculation is outside the design tolerance range, it is determined as a manufacturing defect (abnormality), the pressurizing stand 22 is moved (Step S216) so that the fingerprint input device 100 can be removed from the test device 20A, and the test is completed.

The test device 20A in the present example embodiment as described above uses the test chart 1A to test the optical characteristics of the fingerprint input device 100. The groove portion 2 of the test chart 1A has a resolving power test portion 5 that is formed in a pattern that enables testing of resolving power. In the test device 20A of the present example embodiment, the optical characteristic calculation portion 33 calculates the resolving power of the fingerprint input device 100 based on the shape of the resolving power test portion 5 included in an image. Therefore, according to the test device 20A of the present example embodiment, it is possible to determine that the resolving power of the fingerprint input device 100 meets the design value and is normal.

Fifth Example Embodiment

Figure 11:
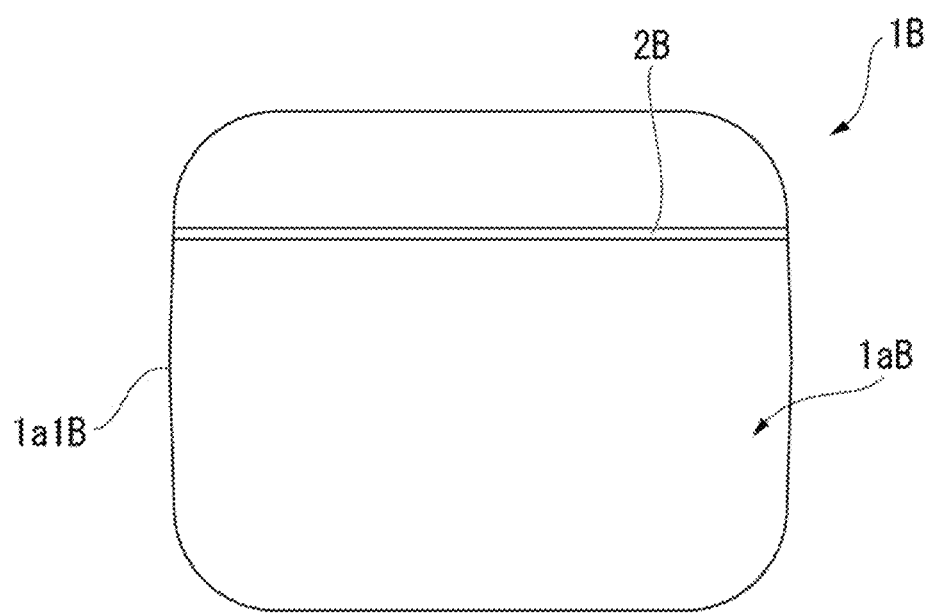
FIG. 11 is a front view of the contact surface of the test chart in the fifth example embodiment of the present disclosure.

Next, the fifth example embodiment of the present disclosure is described referring to FIG. 11. Note that in the description of the present example embodiment, description of those portions similar to those in the first example embodiment mentioned above will be omitted or simplified.

FIG. 11 is a front view of a contact surface 1aB of a test chart 1B of the present example embodiment. As shown in this figure, the contact surface 1aB of the test chart 1B has a groove portion 2B. The contact surface 1aB is a surface that is in contact with the imaging surface 103a of the fingerprint input device 100. The groove portion 2B is provided on the contact surface 103a and connected to an outer edge 1a1B of the contact surface 1aB.

According to the test chart 1B of the present example embodiment, when the contact surface 1aB is pressed against the imaging surface 103a of the fingerprint input device 100, air between the contact surface 1aB and the imaging surface 103a flows through the groove portion 2B and is discharged outside the test chart 1B. Therefore, the test chart 1B of the present example embodiment enables stable optical testing.

Sixth Example Embodiment

The sixth example embodiment of this disclosure is described next. Similar to the test chart 1 of the first example embodiment above, the test chart of the present example embodiment has a contact surface 1a that is brought into contact with the imaging surface 103a of the fingerprint input device 100 described above. Like the test chart 1 of the first example embodiment above, the test chart of the present example embodiment has the groove portion 2 that is provided on the contact surface 1a and connected to the outer edge 1a1 of the contact surface 1a. Therefore, according to the test chart of the present example embodiment, when the contact surface 1a is pressed against the imaging surface 103a of the fingerprint input device 100, air between the contact surface 1a and the imaging surface 103a flows through the groove portion 2 and is discharged outside the test chart. Therefore, the test chart of the present example embodiment enables stable optical testing.

The test chart of the present example embodiment is provided with the groove portion 2 as in the test chart 1 of the first example embodiment above. The groove portion 2 has the frame portion 3 provided in an annular shape and the connection portion 4 connecting the frame portion 3 to the outer edge 1a1 of the contact surface 1a. This allows air between the contact surface 1a and the imaging surface 103a to be discharged and the shape of the frame portion 3, for example, to be used as a pattern for testing optical characteristics.

Seventh Example Embodiment

The seventh example embodiment of this disclosure is described next. Similar to the test chart 1 of the first example embodiment above, the test chart of the present example embodiment has a contact surface 1a that brought into contact with the imaging surface 103a of the fingerprint input device 100 described above. Like the test chart 1 of the first example embodiment above, the test chart of the present example embodiment has the groove portion 2 that is provided on the contact surface 1a and connected to the outer edge 1a1 of the contact surface 1a. Therefore, according to the test chart of the present example embodiment, when the contact surface 1a is pressed against the imaging surface 103a of the fingerprint input device 100, air between the contact surface 1a and the imaging surface 103a flows through the groove portion 2 and is discharged outside the test chart. Therefore, the test chart of the present example embodiment enables stable optical testing.

The test chart of the present example embodiment is provided with the groove portion 2 as in the test chart 1 of the first example embodiment above. The groove portion 2 has the frame portion 3 provided in an annular shape and the connection portion 4 connecting the frame portion 3 to the outer edge 1a1 of the contact surface 1a. This allows air between the contact surface 1a and the imaging surface 103a to be discharged and the shape of the frame portion 3, for example, to be used as a pattern for testing optical characteristics.

The test chart of the present example embodiment is provided with the connection portion 4 as in the test chart 1 of the first example embodiment above. A plurality of the connection portions 4 are provided for the frame portion 3. This allows air to be discharged from the interface between the contact surface 1a and the imaging surface 103a of the fingerprint input device 100 through the respective connection portions 4. Thus, air can be discharged more efficiently and reliably.

Eighth Example Embodiment

The eighth example embodiment of this disclosure is described next. This test chart of the present example embodiment has the groove portion 2A similarly to the test chart 1A of the present example embodiment. The groove portion 2A has the resolving power test portion 5 that is formed in a pattern that enables testing of the resolving power. By testing the optical characteristics of the fingerprint input device 100 using the test chart, it is possible to determine the resolving power of the fingerprint input device 100. For example, if the shape of the resolving power test portion 5 included in the image captured by the fingerprint input device 100 is a shape capable of reproducing the respective line grooves, it is possible to determine that the resolving power of the fingerprint input device 100 is normal and meets the design value.

In this test chart of the present example embodiment, the groove portion 2 may have the frame portion 3 provided in an annular shape and a connection portion 4 connecting the frame portion 3 and the outer edge 1a1 of the contact surface 1a, as in the test chart 1 of the first example embodiment above.

In the test chart of the present example embodiment, as in the test chart 1 of the first example embodiment above, a plurality of the connection portions 4 may be provided for the frame portion 3.

Ninth Example Embodiment

The ninth example embodiment of this disclosure is described next. Similar to the test chart 1 of the first example embodiment above, the test chart of the present example embodiment has the contact surface 1a that is brought into contact with the imaging surface 103a of the fingerprint input device 100 described above. Like the test chart 1 of the first example embodiment above, the test chart of the present example embodiment has the groove portion 2 that is provided on the contact surface 1a and connected to the outer edge 1a1 of the contact surface 1a. Therefore, according to the test chart of the present example embodiment, when the contact surface 1a is pressed against the imaging surface 103a of the fingerprint input device 100, air between the contact surface 1a and the imaging surface 103a flows through the groove portion 2 and is discharged outside the test chart. Therefore, the test chart of the present example embodiment enables stable optical testing.

The test chart of the present example embodiment is formed using silicone resin, which has a refractive index close to that of human skin. In other words, the contact surface 1a is formed of silicone resin. This allows clear imaging of the contact surface 1a.

In the test chart of the present example embodiment, the groove portion 2 may have the frame portion 3 provided in an annular shape and a connection portion 4 connecting the frame portion 3 and the outer edge 1a1 of the contact surface 1a, as in the first example embodiment above.

In the test chart of the present example embodiment, as in the first example embodiment above, a plurality of the connection portions 4 may be provided for the frame portion 3.

The test chart of the present example embodiment may also have the resolving power test portion 5 formed in a pattern enabling testing of the resolving power, as in the second example embodiment above.

Tenth Example Embodiment

The tenth example embodiment of this disclosure is described next. Similar to the test device 20 of the second example embodiment above, the test device of the present example embodiment is provided with the image acquisition portion 32 that acquires an image of the contact surface 1*a* captured by the fingerprint input device 100 described above using the test chart 1. Similar to the test device 20 of the second example embodiment above, the test device of the present example embodiment is provided with the optical characteristic calculation portion 33 that calculates the optical characteristic of the fingerprint input device 100 based on the image acquired by the image acquisition portion 32. Furthermore, similar to the test device 20 of the second example embodiment above, the test device of the present example embodiment is provided with the determination portion 35 that determines the state of the fingerprint input device 100 based on the optical characteristic calculated by the optical characteristic calculation portion 33. As explained in the example embodiment above, according to the test chart 1, air between the contact surface 1*a* and the imaging surface 103*a* flows through the groove portion 2 to be discharged to the outside. Therefore, the test device of the present example embodiment enables a stable optical test.

The test chart of other example embodiments, such as the second example embodiment above, may also be used in the test device of the present example embodiment.

Eleventh Example Embodiment

The eleventh example embodiment of this disclosure is described next. Similar to the test device 20 of the second example embodiment above, the test device of the present example embodiment is provided with the image acquisition portion 32 that acquires an image of the contact surface 1*a* captured by the fingerprint input device 100 described above using the test chart 1. Similar to the test device 20 of the second example embodiment above, the test device of the present example embodiment is provided with the optical characteristic calculation portion 33 that calculates the optical characteristic of the fingerprint input device 100 based on the image acquired by the image acquisition portion 32. Furthermore, similar to the test device 20 of the second example embodiment above, the test device of the present example embodiment is provided with the determination portion 35 that determines the state of the fingerprint input device 100 based on the optical characteristic calculated by the optical characteristic calculation portion 33. As explained in the example embodiment above, according to the test chart 1, air between the contact surface 1*a* and the imaging surface 103*a* flows through the groove portion 2 to be discharged to the outside. Therefore, the test device of the present example embodiment enables a stable optical test.

The optical characteristic calculation portion 33 of the test device of the present example embodiment, similar to the test device 20 of the second example embodiment, sets the horizontal center line L1 along the contact surface 1*a* and the vertical center line L2 along the contact surface 1*a* and orthogonal to the horizontal center line L1, based on the position of the groove portion 2 included in the image. Moreover, the optical characteristic calculation portion 33 calculates the optical axis position of the fingerprint input device 100 (the fingerprint imaging camera 104 and the natural image imaging camera 105) based on the intersection position of the horizontal center line L1 and the vertical center line L2, as an optical characteristic. Therefore, according to the test device of the present example embodiment, it is possible to calculate the optical axis position by simple image processing.

The test chart of other example embodiments, such as the second example embodiment above, may also be used in the test device of the present example embodiment.

Twelfth Example Embodiment

The twelfth example embodiment of this disclosure is described next. Similar to the test device 20 of the second example embodiment above, the test device of the present example embodiment is provided with the image acquisition portion 32 that acquires an image of the contact surface 1*a* captured by the fingerprint input device 100 described above using the test chart 1. Similar to the test device 20 of the second example embodiment above, the test device of the present example embodiment is provided with the optical characteristic calculation portion 33 that calculates the optical characteristic of the fingerprint input device 100 based on the image acquired by the image acquisition portion 32. Furthermore, similar to the test device 20 of the second example embodiment above, the test device of the present example embodiment is provided with the determination portion 35 that determines the state of the fingerprint input device 100 based on the optical characteristic calculated by the optical characteristic calculation portion 33. As explained in the example embodiment above, according to the test chart 1, air between the contact surface 1*a* and the imaging surface 103*a* flows through the groove portion 2 to be discharged to the outside. Therefore, the test device of the present example embodiment enables a stable optical test.

In the test device of the present example embodiment, similar to the test device 20 of the second example embodiment, the optical characteristic calculation portion 33 calculates the angle of view of the fingerprint input device 100 (fingerprint imaging camera 104 and natural image imaging camera 105) based on the length dimensions of the horizontal center line L1 and the vertical center line L2, as an optical characteristic. Therefore, according to this test device 20 of the present example embodiment, it is possible to calculate the angle of view with simple image processing.

Note that the optical characteristic calculation portion 33 of the test device of the present example embodiment, similar to the test device 20 of the second example embodiment, may set the horizontal center line L1 along the contact surface 1*a* and the vertical center line L2 along the contact surface 1*a* and orthogonal to the horizontal center line L1, based on the position of the groove portion 2 included in the image. Moreover, the optical characteristic calculation portion 33 may calculate the optical axis position of the fingerprint input device 100 (the fingerprint imaging camera 104 and the natural image imaging camera 105) based on the intersection position of the horizontal center line L1 and the vertical center line L2, as an optical characteristic.

The test chart of other example embodiments, such as the second example embodiment above, may also be used in the test device of the present example embodiment.

Thirteenth Example Embodiment

The thirteenth example embodiment of this disclosure is described next. Similar to the test device 20A of the fourth example embodiment above, the test device of the present example embodiment is provided with the image acquisition portion 32 that acquires an image of the contact surface 1*a* captured by the fingerprint input device 100 described above using the test chart 1A. Similar to the test device 20A of the fourth example embodiment above, the test device of the present example embodiment is provided with the optical characteristic calculation portion 33 that calculates the optical characteristic of the fingerprint input device 100 based on the image acquired by the image acquisition portion 32. Furthermore, similar to the test device 20A of the fourth example embodiment above, the test device of the present example embodiment is provided with the determination portion 35 that determines the state of the fingerprint input device 100 based on the optical characteristic calculated by the optical characteristic calculation portion 33. As explained in the example embodiment above, according to the test chart 1A, air between the contact surface 1aA and the imaging surface 103a flows through the groove portion 2A to be discharged to the outside. Therefore, the test device of the present example embodiment enables a stable optical test.

The test device in the present example embodiment uses the test chart 1A to test the optical characteristics of the fingerprint input device 100. The groove portion 2A of the test chart 1A has a resolving power test portion 5 that is formed in a pattern that enables testing of resolving power. In the test device of the present example embodiment, the optical characteristic calculation portion 33 calculates the resolving power of the fingerprint input device 100 based on the shape of the resolving power test portion 5 included in an image. Therefore, according to the test device of the present example embodiment, it is possible to determine that the resolving power of the fingerprint input device 100 meets the design value and is normal.

Note that the optical characteristic calculation portion 33 of the present example embodiment may set the horizontal center line L1 along the contact surface 1aA and the vertical center line L2 along the contact surface 1aA and orthogonal to the horizontal center line L1, based on the position of the groove portion 2A included in the image.

The optical characteristic calculation portion 33 of the present example embodiment may calculate the angle of view of the fingerprint input device 100 (fingerprint imaging camera 104 and natural image imaging camera 105) based on the length dimensions of the horizontal center line L1 and the vertical center line L2, as an optical characteristic.

Fourteenth Example Embodiment

The fourteenth example embodiment of this disclosure is described next. Similar to the test device 20 of the second example embodiment above, the test device of the present example embodiment is provided with the image acquisition portion 32 that acquires an image of the contact surface 1a captured by the fingerprint input device 100 described above using the test chart 1. Similar to the test device 20 of the second example embodiment above, the test device of the present example embodiment is provided with the optical characteristic calculation portion 33 that calculates the optical characteristic of the fingerprint input device 100 based on the image acquired by the image acquisition portion 32. Furthermore, similar to the test device 20 of the second example embodiment above, the test device of the present example embodiment is provided with the determination portion 35 that determines the state of the fingerprint input device 100 based on the optical characteristic calculated by the optical characteristic calculation portion 33. As explained in the example embodiment above, according to the test chart 1, air between the contact surface 1a and the imaging surface 103a flows through the groove portion 2 to be discharged to the outside. Therefore, the test device of the present example embodiment enables a stable optical test.

The test device of the present example embodiment, like the test device 20 of the second example embodiment, is equipped with an installation stand 21 that fixes the fingerprint input device 100 and a pressing portion 26 that presses the contact surface 1a of the test chart 1 onto the imaging surface 103a of the fingerprint input device 100. Therefore, according to the test device, it is possible to reliably discharge air from the contact area between the imaging surface 103a of the fingerprint input device 100 and the contact surface 1a of the test chart 1.

Note that the optical characteristic calculation portion 33 of the present example embodiment may set the horizontal center line L1 along the contact surface 1a and the vertical center line L2 along the contact surface 1a and orthogonal to the horizontal center line L1, based on the position of the groove portion 2 included in the image.

The optical characteristic calculation portion 33 of the present example embodiment may calculate the angle of view of the fingerprint input device 100 (fingerprint imaging camera 104 and natural image imaging camera 105) based on the length dimensions of the horizontal center line L1 and the vertical center line L2, as an optical characteristic.

The test chart of other example embodiments, such as the second example embodiment above, may also be used in the test device of the present example embodiment.

Fifteenth Example Embodiment

The fifteenth example embodiment of this disclosure is described next. Similar to the test device 20 of the second example embodiment above, the test device of the present example embodiment is provided with the image acquisition portion 32 that acquires an image of the contact surface 1a captured by the fingerprint input device 100 described above using the test chart 1. Similar to the test device 20 of the second example embodiment above, the test device of the present example embodiment is provided with the optical characteristic calculation portion 33 that calculates the optical characteristic of the fingerprint input device 100 based on the image acquired by the image acquisition portion 32. Furthermore, similar to the test device 20 of the second example embodiment above, the test device of the present example embodiment is provided with the determination portion 35 that determines the state of the fingerprint input device 100 based on the optical characteristic calculated by the optical characteristic calculation portion 33. As explained in the example embodiment above, according to the test chart 1, air between the contact surface 1a and the imaging surface 103a flows through the groove portion 2 to be discharged to the outside. Therefore, the test device of the present example embodiment enables a stable optical test.

The test device of the present example embodiment, like the test device 20 of the second example embodiment, is equipped with an installation stand 21 that fixes the fingerprint input device 100 and a pressing portion 26 that presses the contact surface 1a of the test chart 1 onto the imaging surface 103a of the fingerprint input device 100. Therefore, according to the test device, it is possible to reliably discharge air from the contact area between the imaging surface 103a of the fingerprint input device 100 and the contact surface 1a of the test chart 1.

The pressing portion 26 of the present example embodiment is provided with the pressurizing stand 22 that is in contact with the test chart 1 from above, the weight 23 supported by the pressurizing stand 22, and the actuator 24 that supports the pressurizing stand 22 in a vertically adjustable manner. This allows the pressurizing stand 22 to be easily raised and lowered using the power of the actuator 24. The amount of pressure (pressing force) on the test chart 1 can be easily adjusted by adjusting the support force of the pressurizing stand 22 by the actuator 24.

The test chart of other example embodiments, such as the second example embodiment above, may also be used in the test device of the present example embodiment.

Although this disclosure has been described above using example embodiments, the technical scope of this disclosure is not limited to the scope described in the above example embodiments. It is clear to those skilled in the art that various changes or improvements can be made to the above example embodiments. It is clear from the claims that example embodiments with such modifications or improvements may also be included within the technical scope of this disclosure.

Some or all of the above example embodiments may also be described as, but not limited to, the following supplementary notes.

(Supplementary Note 1) A test jig characterized by having a contact surface that is brought into contact with an imaging surface of a skin pattern input device, and a groove portion that is provided on the contact surface and connected to the outer edge of the contact surface.

(Supplementary Note 2) The test jig according to Supplementary Note 1, wherein the groove portion has an annular portion provided in an annular shape; and a connection portion that connects the annular portion and the outer edge of the contact surface.

(Supplementary Note 3) The test jig according to Supplementary Note 2, characterized by a plurality of the connection portions being provided with respect to the annular portion.

(Supplementary Note 4) The test jig according to any one of Supplementary Notes 1 to 3, wherein the groove portion has a resolving power test portion formed in a pattern that enables testing of resolving power.

(Supplementary Note 5) The test jig according to any one of Supplementary Notes 1 to 4, wherein at least the contact surface is formed using silicone resin.

(Supplementary Note 6) A test device characterized by being provided with: an image acquisition means that acquires an image of the contact surface captured by a skin pattern input device using the test jig according to any one of Supplementary Notes 1 to 5; an optical characteristic calculation means that calculates an optical characteristic of the skin pattern input device based on the image acquired by the image acquisition means; and a determination means that determines the state of the skin pattern input device based on the optical characteristic calculated by the optical characteristic calculation means.

(Supplementary Note 7) The test device according to Supplementary Note 6, wherein the optical characteristic calculation means defines a first reference line along the contact surface and a second reference line along the contact surface and orthogonal to the first reference line based on a position of the groove portion included in the image, and calculates an optical axis position of the skin pattern input device based on the intersection position of the first reference line and the second reference line as at least one of the optical characteristics.

(Supplementary Note 8) The test device according to Supplementary Note 6 or 7, wherein the optical characteristic calculation means defines a first reference line along the contact surface and a second reference line along the contact surface and orthogonal to the first reference line based on the position of the groove portion included in the image, and calculates the angle of view of the skin pattern input device based on the length dimension of the first reference line and the length dimension of the second reference line as at least one of the optical characteristics.

(Supplementary Note 9) The test device according to any one of Supplementary Notes 6 to 8, wherein the groove portion of the test jig has a resolving power test portion formed in a pattern that enables testing of resolving power; and the optical characteristic calculation means calculates the resolving power of the skin pattern input device as at least one of the optical characteristics based on the shape of the resolving power test portion included in the image.

(Supplementary Note 10) The test device according to any one of Supplementary Notes 6 to 9, characterized by being provided with: a fixing means that fixes the skin pattern input device; and a pressing means that presses the contact surface of the test jig against the imaging surface of the skin pattern input device.

(Supplementary Note 11) The test device according to Supplementary Note 10, The pressing means is characterized in that it is equipped with a pressurizing stand that is in contact with the test jig from above, a weight supported by the pressurizing stand, and an actuator that supports the pressurizing stand in an elevating and lowering manner.

(Supplementary Note 12) A test method in which a test jig has a contact surface that is brought into contact with an imaging surface of a skin pattern input device, and a groove portion that is provided on the contact surface and connected to the outer edge of the contact surface, the method acquiring an image of the contact surface captured by a skin pattern input device using the test jig; calculating an optical characteristic of the skin pattern input device based on the image; and determining the state of the skin pattern input device based on the optical characteristic.

INDUSTRIAL APPLICABILITY

According to one of the above-mentioned example aspects, stable optical test can be performed for skin pattern input devices.

DESCRIPTION OF REFERENCE SIGNS

1 Test chart (test jig)
1a Contact surface
1A Test chart (test jig)
1a1 Outer edge
1a1B Outer edge
1aA Contact surface
1aB Contact surface
1b Peripheral surface
1B Test chart (test jig)
2 Groove portion
2A Groove portion
2B Groove portion
3 Frame portion (annular portion)
3a First long side
3b Second long side
3c First short side
3d Second short side
4 Connection portion
5 Resolving power test portion
10 Test system
10A Test System
20 Test device
20A Test device
21 Installation stand (fixing means)

22 Pressurizing stand
23 Weight
24 Actuator
25 Control operation portion
25A Control operation portion
26 Pressing portion (pressing means)
30 Actuator control portion
31 Fingerprint input device control portion
32 Image acquisition portion (image acquisition means)
33 Optical characteristic calculation portion (optical characteristic calculation means)
34 Storage portion
35 Determination portion (determination means)
100 Fingerprint input device (skin pattern input device)
101 White light LED substrate
102 Near-infrared light LED substrate
103 Prism
103a Imaging surface
103b Facing surface
103c Intersecting surface
103d Surface
104 Fingerprint imaging camera
105 Natural image imaging camera
106 Control substrate
107 Light guide
L1 Horizontal center line (first reference line)
L2 Vertical center line (second reference line)
R Central region

What is claimed is:

1. A test jig comprising:
a contact surface that is brought into contact with an imaging surface of a skin pattern input device; and
a groove portion that is provided on the contact surface and connected to the outer edge of the contact surface.

2. The test jig according to claim 1, wherein the groove portion comprises:
an annular portion provided in an annular shape; and
a connection portion that connects the annular portion and the outer edge of the contact surface.

3. The test jig according to claim 2, wherein a plurality of the connection portions are provided with respect to the annular portion.

4. The test jig according to claim 1, wherein the groove portion has a resolving power test portion formed in a pattern that enables testing of resolving power.

5. The test jig according to claim 1, wherein at least the contact surface is formed using silicone resin.

6. A test device comprising:
at least one memory configured to store instructions; and
at least one processor configured to execute the instructions to:
acquire an image of the contact surface captured by a skin pattern input device using the test jig according to claim 1;
calculate an optical characteristic of the skin pattern input device based on the acquired image; and
determine the state of the skin pattern input device based on the calculated optical characteristic.

7. The test device according to claim 6, wherein the at least one processor is configured to execute the instructions to:
define a first reference line along the contact surface and a second reference line along the contact surface and orthogonal to the first reference line based on a position of the groove portion included in the image, and
calculate an optical axis position of the skin pattern input device based on the intersection position of the first reference line and the second reference line as at least one of the optical characteristics.

8. The test device according to claim 6, wherein the at least one processor is configured to execute the instructions to:
define a first reference line along the contact surface and a second reference line along the contact surface and orthogonal to the first reference line based on the position of the groove portion included in the image, and
calculate the angle of view of the skin pattern input device based on the length dimension of the first reference line and the length dimension of the second reference line as at least one of the optical characteristics.

9. The test device according to claim 6, wherein the groove portion of the test jig has a resolving power test portion formed in a pattern that enables testing of resolving power, and
wherein the at least one processor is configured to execute the instructions to calculate the resolving power of the skin pattern input device as at least one of the optical characteristics based on the shape of the resolving power test portion included in the image.

10. The test device according to claim 6, comprising: an installation stand that fixes the skin pattern input device; and
a pressing portion that presses the contact surface of the test jig against the imaging surface of the skin pattern input device.

11. The test device according to claim 10, wherein the pressing portion comprises:
a pressurizing stand that is in contact with the test jig from above;
a weight supported by the pressurizing stand; and
an actuator that supports the pressurizing stand in an elevatable manner.

12. A test method wherein a test jig has a contact surface that is brought into contact with an imaging surface of a skin pattern input device, and a groove portion that is provided on the contact surface and connected to the outer edge of the contact surface, the method comprising:
acquiring an image of the contact surface captured by a skin pattern input skin pattern input device using the test jig;
calculating an optical characteristic of the skin pattern input device based on the image; and
determining the state of the skin pattern input device based on the optical characteristic.

* * * * *